(12) United States Patent
Hallinan et al.

(10) Patent No.: US 10,584,087 B2
(45) Date of Patent: Mar. 10, 2020

(54) REMOVAL OF PERMANGANATE REDUCING COMPOUNDS FROM INTERMEDIATE GAA PROCESS STREAMS

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyls, LLC, Houston, TX (US)

(*) Notice: Subject to any disclaimer, the term of this patent is extended or adjusted under 35 U.S.C. 154(b) by 0 days.

(21) Appl. No.: 16/362,245

(22) Filed: Mar. 22, 2019

(65) Prior Publication Data

US 2019/0292124 A1    Sep. 26, 2019

Related U.S. Application Data

(60) Provisional application No. 62/647,378, filed on Mar. 23, 2018.

(51) Int. Cl.
*C07C 51/12* (2006.01)
*C07C 53/00* (2006.01)
*C07C 53/08* (2006.01)
*C07C 51/47* (2006.01)
*C07C 51/44* (2006.01)

(52) U.S. Cl.
CPC ............. *C07C 51/12* (2013.01); *C07C 51/44* (2013.01); *C07C 51/47* (2013.01); *C07C 53/08* (2013.01)

(58) Field of Classification Search
CPC .................................. C07C 51/12; C07C 53/08
See application file for complete search history.

(56) References Cited

U.S. PATENT DOCUMENTS

| | | |
|---|---|---|
| 5,932,764 A | 8/1999 | Morris et al. |
| 6,552,221 B1 | 4/2003 | Hallinan et al. |
| 7,223,886 B2 | 5/2007 | Scates et al. |
| 7,683,212 B2 | 3/2010 | Kojima et al. |
| 8,293,534 B2 | 10/2012 | Hallinan |
| 8,940,932 B2 | 1/2015 | Shimizu |
| 8,969,613 B2 | 3/2015 | Hallinan et al. |
| 9,056,825 B2 | 6/2015 | Torrence et al. |
| 9,216,936 B2 | 12/2015 | Torrence et al. |
| 9,561,994 B2 * | 2/2017 | Shaver .................. C07C 51/12 |
| 9,822,055 B2 | 11/2017 | Ramage et al. |
| 2008/0051601 A1 | 2/2008 | Sawyer et al. |
| 2014/0121404 A1 | 5/2014 | Hallinan et al. |
| 2016/0121320 A1 | 5/2016 | You et al. |
| 2016/0289153 A1 | 10/2016 | Scates et al. |
| 2016/0376213 A1 | 12/2016 | Ramage et al. |
| 2017/0158592 A1 | 6/2017 | Hallinan et al. |
| 2017/0158596 A1 | 6/2017 | Hallinan et al. |

FOREIGN PATENT DOCUMENTS

| | | |
|---|---|---|
| WO | 2008024198 A1 | 2/2008 |
| WO | 2014070739 A1 | 5/2014 |
| WO | 2017096235 A1 | 6/2017 |
| WO | 2017096255 A1 | 6/2017 |

OTHER PUBLICATIONS

The International Search Report and The Written Opinion for PCT/US2019/023691 dated May 13, 2019.

* cited by examiner

*Primary Examiner* — Sikarl A Witherspoon

(57) ABSTRACT

A method of producing acetic acid, the method comprising: reacting methanol and/or methanol derivatives with carbon monoxide in the presence of a liquid reaction medium under carbonylation conditions to form a carbonylation product comprising acetic acid and one or more oxidizable impurities; and contacting at least a portion of the carbonylation product or a derivative thereof with an adsorbent at adsorption conditions to provide a purified product comprising a reduced concentration of at least one of the one or more oxidizable impurities relative to a concentration thereof in the at least a portion of the carbonylation product or the derivative thereof. A system for carrying out the method is also provided.

20 Claims, 3 Drawing Sheets

REMOVAL OF PERMANGANATE REDUCING COMPOUNDS FROM INTERMEDIATE GAA PROCESS STREAMS

CROSS-REFERENCE TO RELATED APPLICATIONS

This application claims the benefit of priority to U.S. Provisional Patent Application No. 62/647,378, filed on Mar. 23, 2018, which is incorporated herein by reference in its entirety.

TECHNICAL FIELD

This disclosure relates to the production of acetic acid and related processes. More specifically, this disclosure relates to the removal of impurities within such processes. Still more specifically, this disclosure relates to the removal of oxidizable impurities from intermediate streams comprising water and weight percent (wt %) levels of oxidizable impurities.

BACKGROUND

Carboxylic acids, such as acetic acid, may be commercially produced by alcohol carbonylation. Unfortunately, carbonylation processes create unwanted byproducts. Significant energy has been devoted to the removal of such byproducts, including a variety of processes and techniques. However, such processes and techniques can be complicated and costly.

Permanganate time (PT) is a quality test used industry wide for glacial acetic acid (GAA). The PT test can be utilized to determine the amount of oxidizable impurities present in a GAA product comprising low levels (e.g., less than or equal to 2000 ppm) of oxidizable impurities. Oxidizable impurities or 'permanganate reducing compounds' (PRCs), include, without limitation, saturated and unsaturated carbonyl compounds including acetaldehyde, acetone, crotonaldehyde, 2-ethyl crotonaldehyde and associated aldol condensation products. In contrast to GAA product which contains ppm levels of oxidizable impurities, intermediate process streams such as decanter light or heavy phases, may contain weight percent levels of these impurities. Some methods attempt removal of permanganate reducing compounds from decanter light or heavy phases via techniques such as oxidation or multiple distillation and/or aqueous extraction. Others describe removal of such compounds via pressure distillation or the addition of extra distillation columns. Other methods involve utilizing permanganate itself as a reducing agent in the process where aqueous or silica-supported $KMnO_4$ added to the bottom of a distillation column is employed to remove oxidizable impurities such as acetaldehyde and crotonaldehyde. In addition to removal methods, various control methods have been proposed where the purpose is to limit the formation of acetaldehyde in the carbonylation reactor. Some such methods indicate a 25% improvement in permanganate time of a so-produced GAA product.

Conventional systems and methods for the removal of oxidizable impurities/PRCs from carboxylic acids can be costly and/or time consuming. Accordingly, a need exists for improved systems and methods for improving the permanganate time (oxidizable impurity content) of GAA without the need for conventionally employed removal methods and associated drawbacks. Disclosed herein are embodiments directed to providing such systems and methods.

SUMMARY

Herein disclosed is a method of producing acetic acid, the method comprising: reacting methanol and/or methanol derivatives with carbon monoxide in the presence of a liquid reaction medium under carbonylation conditions to form a carbonylation product comprising acetic acid and one or more oxidizable impurities; and contacting at least a portion of the carbonylation product or a derivative thereof with an adsorbent at adsorption conditions to provide a purified product comprising a reduced concentration of at least one of the one or more oxidizable impurities relative to a concentration thereof in the at least a portion of the carbonylation product or the derivative thereof.

Also disclosed herein is an acetic acid production system comprising: a carbonylation reactor for contacting methanol with carbon monoxide in the presence of a liquid reaction medium under carbonylation conditions to form a carbonylation product comprising acetic acid and one or more oxidizable impurities; and an adsorbent vessel in which at least a portion of the carbonylation product or a derivative thereof can be contacted with an adsorbent at adsorption conditions to provide a purified product having a reduced concentration of at least one of the one or more oxidizable impurities relative to a concentration thereof in the at least a portion of the carbonylation product or the derivative thereof.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DETAILED DESCRIPTION

Figure 1:
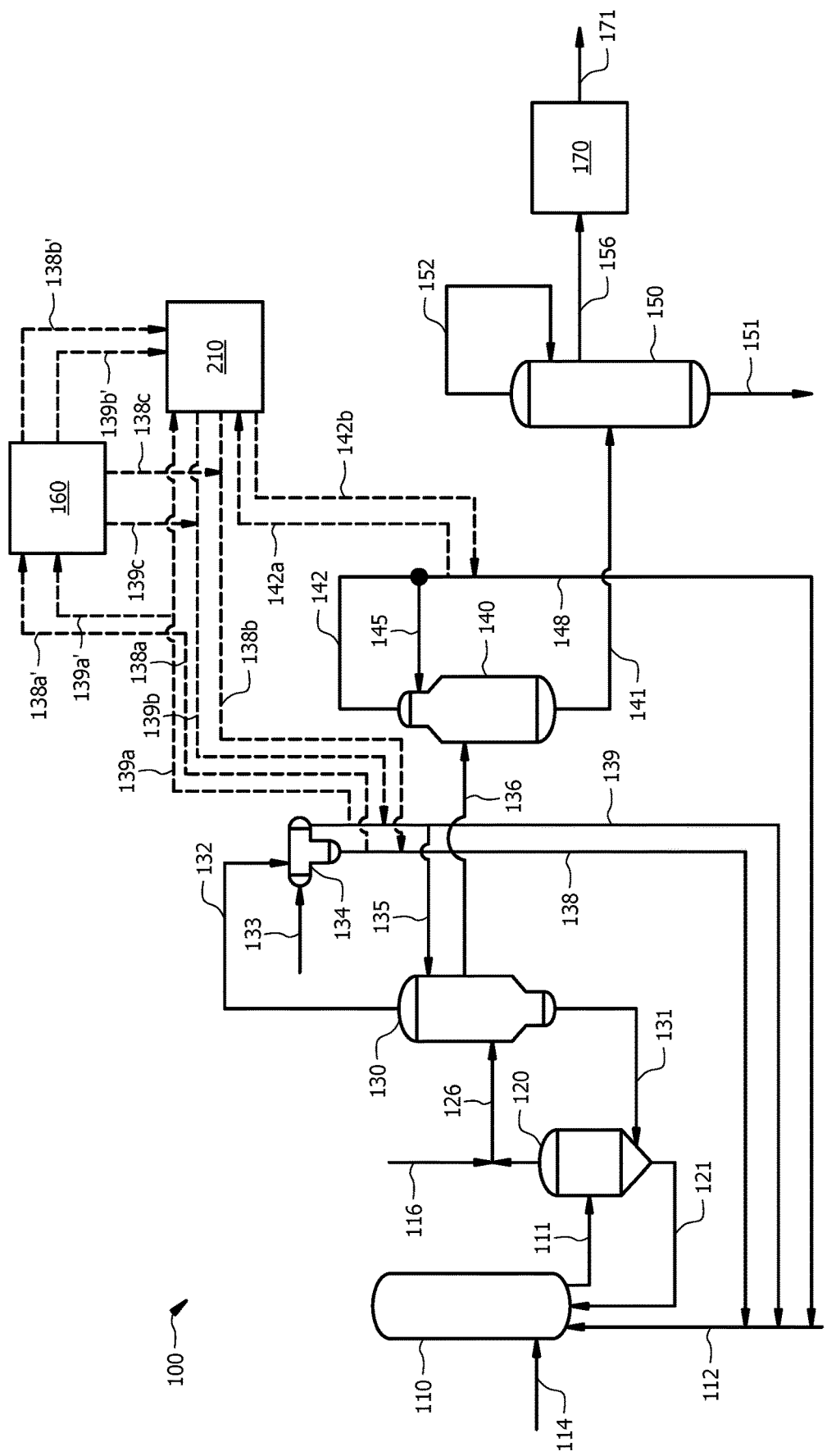
FIG. 1 is a schematic of a carboxylic acid production system 100, according to an embodiment of this disclosure.

This disclosure relates to systems and methods for the removal of oxidizable impurities, such as acetaldehyde and crotonaldehyde, at up to weight percent (wt %) levels from aqueous intermediate streams encountered during the production of carboxylic acid. The terms 'oxidizable impurities' and 'permanganate reducing compounds' (or 'PRCs') are used interchangeably herein. U.S. Provisional Patent Application No. 62/647,355 entitled Improved Method for Purification of GAA, describes the improvement in permanganate time of a purified, low water GAA product, containing ppm level oxidizable impurities, by contact with an acidic ion exchange resin such as AMBERLYST® 15, which improvement increases at elevated temperatures (e.g., above 70° C.). Other materials, such as zeolites and carbons, showed little efficiency in this regard, and the removal of PRCs from the GAA product was hindered in the presence of substantial amounts of water. It has been unexpectedly discovered that some adsorbents, such as nanozeolites, can, however, be utilized to remove oxidizable impurities (such as acetaldehyde and crotonaldehyde) at the wt % level from aqueous streams which may be intermediate streams in an acetic acid production process, rather than highly purified acetic acid product streams. Without being bound by theory, it is noted that, due to higher boiling point and a resulting ability to get further downstream, GAA product will contain a higher ppm concentration of crotonaldehyde relative to acetaldehyde, while the reverse is true for intermediate streams, where acetaldehyde will be present in a higher concentration. Furthermore, the removal of PRCs (which is slower and improves with higher temperatures in GAA product solutions with strongly acidic ion exchangers) can occur essentially instantly (e.g., be substantially complete within a minute) at room temperature in aqueous solution with the adsorbents described herein.

This disclosure relates to systems and methods for the removal of oxidizable impurities at up to wt % levels from an aqueous intermediate stream produced during carboxylic acid production via contact thereof with an adsorbent. In embodiments, the carboxylic acid is glacial acetic acid. Embodiments described herein thus include processes for producing acetic acid. Furthermore, embodiments include production of glacial acetic acid (which is encompassed by the term "acetic acid" as referenced herein). Glacial acetic acid refers to acetic acid that is often undiluted (e.g., includes a water concentration of less than or equal to 0.15 wt % based on the total weight of acetic acid and water). In embodiments, the acetic acid production processes may include carbonylation processes. For example (and for purposes of discussion herein), the acetic acid production processes may include the carbonylation of methanol and/or its derivatives to produce acetic acid. Thus, while suitable for removing oxidizable impurities from various aqueous streams produced during the production of carboxylic acid, description will be made hereinbelow with reference to the removal of oxidizable impurities from aqueous intermediate streams produced during the production of GAA.

The aqueous intermediate stream contacted with the adsorbent as per this disclosure may be referred to herein as a portion of a carbonylation product or a derivative thereof. Although sometimes referred to as an intermediate acetic acid stream, the stream contacted with the adsorbent according to this disclosure can, in embodiments, comprise primarily water and oxidizable impurities (e.g., can comprise less than or equal to 10 wt % acetic acid, or even less).

In embodiments, the aqueous intermediate carboxylic acid (e.g., acetic acid) stream treated according to this disclosure can comprise at least 30, 40, 50, 60, 70, 80, 85, or even greater, wt % water, and may comprise less than or equal to 70, 60, 50, 40, 30, 20, 10, or less, wt % carboxylic acid (e.g., acetic acid). The aqueous intermediate stream can comprise oxidizable impurities to be removed via the adsorbent, and, in embodiments, can comprise weight percent levels of one or more oxidizable impurities. As utilized herein, weight percent levels of one or more oxidizable impurities can indicate greater than or equal to 0.5 wt % levels. The amount of oxidizable impurities may be determined via Fourier-transform infrared spectroscopy (FTIR) and/or gas chromatography (GC).

The oxidizable impurities can comprise saturated carbonyl compounds, unsaturated carbonyl compounds, aldol condensation products thereof, propionic acid, or combinations thereof. In embodiments, the oxidizable impurities comprise acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof. In embodiments, the aqueous intermediate stream contacted with adsorbent comprises greater than or equal to 0.02, 0.05, 0.1, 0.25, or 0.5 wt % of such oxidizable impurities, based on the total weight of the aqueous intermediate stream. Without limitation, such oxidizable impurities/PRCs can include acetaldehyde, acetone, methyl ethyl ketone, butyraldehyde, crotonaldehyde, 2-ethyl crotonaldehyde, 2-ethyl butyraldehyde, aldol condensation products thereof, or combinations thereof. In embodiments, the aqueous intermediate stream contacted with the adsorbent comprises at least 0.05, 10, or 50 wt % of oxidizable impurities, based on the total weight of the aqueous intermediate stream. The oxidizable impurities may comprise primarily acetaldehyde, and/or crotonaldehyde.

In embodiments, the aqueous intermediate stream contacted with the adsorbent as per this disclosure comprises greater than or equal to 0.02, 0.5, 2 or 10 wt % of such oxidizable impurities, based on the total weight of the aqueous intermediate stream, and the treated aqueous intermediate stream or purified product obtained via contact with the adsorbent as described herein comprises less than or equal to 0.01, 1, or 3 wt % of such oxidizable impurities. In embodiments, the at least a portion of the carbonylation product or the derivative thereof contacted with the adsorbent comprises at least 0.05, 10, or 50 wt % oxidizable impurities, and the purified product comprises less than or equal to 0.01, 3, or 20 wt % oxidizable impurities. In embodiments, the purified product comprises at least 10, 20, 30, 40, 50, 60, 70, or 80 percent less oxidizable impurities than the aqueous intermediate stream contacted with the adsorbent Illustrative embodiments of the subject matter claimed below will now be disclosed. In the interest of clarity, not all features of an actual implementation are described in this specification. It will be appreciated that in the development of any such actual embodiment, numerous implementation-specific decisions can be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range. As used herein, a 'majority' refers to greater than 50 weight percent.

Further, in the description below, unless otherwise specified, the compounds described herein may be substituted or unsubstituted and the listing of compounds may include derivatives thereof.

The aqueous intermediate stream treated by contacting thereof with an adsorbent according to the herein disclosed system and method can be produced via any systems and methods known in the art. Description of a system and method of this disclosure will now be made with reference to FIG. 1, which illustrates a schematic of a specific, non-limiting embodiment of a carboxylic acid production system 100 comprising adsorbent vessel 210 and exemplary apparatus for producing the aqueous intermediate stream to be treated therein.

Carboxylic acid production system 100 comprises a reactor 110, a flash vessel 120, equipment associated with the reactor 110 and flash vessel 120, and streams associated with the reactor 110 and the flash vessel 120, for example, streams (or portions of streams) 111, 112, 114, 121, 126, 131, 116, 138, 139 and 148. Reactor 110 is a reactor or vessel in which an alcohol is carbonylated in the presence of a carbonylation catalyst to form a carboxylic acid at elevated pressure and temperature. Flash vessel 120 is a tank or vessel in which a reaction mixture obtained in the reactor, for example reactor 110, is at least partially depressurized and/or cooled to form a vapor stream and a liquid stream.

A carboxylic acid production system may further comprise a light-ends column 130, equipment associated with light-ends column 130, such as decanter 134, and streams associated with the light-ends column 130 and/or decanter 134, such as, for example, streams 116, 126, 131, 132, 133, 135, 136, 138 and 139. Light-ends column 130 is a fractioning or distillation column and includes any equipment associated with the column, including but not limited to heat exchangers, decanters, pumps, compressors, valves, and the like.

A carboxylic acid production system may further comprise a drying column 140, a heavy-ends column 150, an organic iodide-removal apparatus 170, equipment associated with drying column 140, heavy-ends column 150, and/or organic iodide-removal apparatus, and streams associated with drying column 140, heavy-ends column 150, and/or organic-iodide-removal apparatus 170. For example, carboxylic acid production system 100 comprises drying column 140, heavy-ends column 150, organic iodide-removal apparatus 170, and streams 136, 141, 142, 145, 148, 151, 152, 156 and 171. Heavy-ends column 150 can be a fractioning or distillation column and includes any equipment associated with the column, including but not limited to heat exchangers, decanters, pumps, compressors and valves.

A carboxylic acid production system may include process streams recycled to reactor 110, flash vessel 120, light-ends column 130, and/or decanter 134, such as, for example, streams 121, 138, 139 and 148.

The carbonylation processes utilized to produce acetic acid within reactor 110 may include reacting an alcohol, such as methanol and/or methanol derivative(s), with carbon monoxide in the presence of a reaction medium, such as a liquid reaction medium, under carbonylation conditions sufficient to form a carbonylation product including acetic acid, and recovering the formed acetic acid from the carbonylation product. In embodiments, reactor 110 may thus be configured to receive a carbon monoxide feed stream 114 and a methanol or methanol/methyl acetate feed stream 112. A reaction mixture may be withdrawn from reactor 110 via stream 111. Other streams may be included, for example, a stream that may recycle a bottoms mixture of reactor 110 back into reactor 110, or a stream may be included to release a gas from reactor 110. Stream 111 may include at least a part of the reaction mixture.

As described herein, the term "liquid reaction medium" refers to a reaction medium that is primarily liquid in form. For example, the liquid reaction medium contains minor amounts of alternative phases. In one or more embodiments, the liquid reaction medium is at least 90%, or at least 91%, or at least 92%, or at least 93%, or at least 94%, or at least 95%, or at least 96%, or at least 97%, or at least 98%, or at least 99% liquid phase.

The reaction medium includes a carbonylation catalyst. Carbonylation catalysts may include, but are not limited to, rhodium catalysts, iridium catalysts and palladium catalysts. Rhodium catalysts may include rhodium metal and rhodium compounds selected from rhodium salts, rhodium oxides, rhodium acetates, rhodium phosphates, organo-rhodium compounds, coordination compounds of rhodium, or a combination thereof (See, U.S. Pat. No. 5,817,869, which is hereby incorporated herein in its entirety for purposes not contrary to this disclosure). Iridium catalysts may include iridium metal and iridium compounds selected from iridium acetates, iridium oxalates, iridium acetoacetates, or a combination thereof (see, for example, U.S. Pat. No. 5,932,764, which is hereby incorporated herein in its entirety for purposes not contrary to this disclosure).

In embodiments, the carbonylation catalyst is a transition metal catalyst, such as a rhodium catalyst. It is contemplated that any rhodium carbonylation catalyst may be used in the carbonylation process described herein. In embodiments, the rhodium catalyst comprises a rhodium source selected from rhodium metal, rhodium halides, rhodium oxide, rhodium acetate, organo-rhodium compounds, coordination compounds of rhodium, or similar rhodium compounds. Additionally, mixtures of different rhodium sources may also be used. Non-limiting examples of rhodium sources which can be used in the carbonylation process include $RhCl_3$, $RhBr_3$, $RhI_3$, $RhCl_3 \cdot 3H_2O$, $RhBr_3 \cdot 3H_2O$, $RhI_3 \cdot 3H_2O$, $Rh_2(CO)_4Cl_2$, $Rh_2(CO)_4Br_2$, $Rh_2(CO)_4I_2$, $Rh_2(CO)_8$, $Rh(CH_3CO_2)_2$, $Rh(CH_3CO_2)_3$, $Rh[(C_6H_5)_3P]_2(CO)I$, $Rh[(C_6H_5)_3P]_2(CO)Cl$, elemental Rh, $Rh(NO_3)_3$, $Rh(SnCl_3)[(C_6H_5)P]_2$, $RhCl(CO)[(C_6H_5)As]_2$, $RhI(CO)[(C_6H_5)Sb]_2$, $Rh[(C_6H_5)_3P]_2(CO)Br$, $Rh[(n-C_4H_9)_3P]_2(CO)Br$, $Rh[(n-C_4H_9)_3P]_2(CO)I$, $RhBr[(C_6H_5)_3P]_3$, $RhI[(C_6H_5)_3P]_3$, $RhCl[(C_6H_5)_3P]_3$, $RhCl[(C_6H_5)_3P]_3H_2$, $[(C_6H_5)_3P]_3Rh(CO)H$, $Rh_2O_3$, $[Rh(C_3H_4)_2Cl]_2$, $K_4Rh_2Cl_2(SnCl_2)_4$, $K_4Rh_2Br_2(SnBr_2)_4$, $[H][Rh(CO)_2I_2]$, $K_4Rh_2I_2(SnI_2)_4$, or is a complex of the formula $[Rh(CO)_2 X_2][Y]$, wherein X is a halide and Y is a proton, an alkali metal cation, or a quaternary compound of nitrogen, phosphorus, or arsenic, or is a similar rhodium complex. In embodiments, the rhodium source is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, or $[H][Rh(CO)_2I_2]$. In embodiments, the rhodium source is $Rh(CH_3CO_2)_2$, $Rh(CH_3CO_2)_3$, or $[H][Rh(CO)_2I_2]$.

The rhodium compound or complex may be used in a concentration sufficient to achieve a reasonable amount of carbonylation or an effective rate of carbonylation. Without being bound by theory, excess amounts of the rhodium catalyst can lead to the undesired byproducts. Thus, the optimization of the rhodium catalyst is one factor which can directly impact the rate, amount, and yield of the carbonylation product. In a carbonylation process, the concentration of the rhodium catalyst that may be used is from 10 ppm to 10,000 ppm, including from 200 ppm to 1200 ppm and 400 ppm to 1000 ppm. These concentrations can also be expressed using molarity. In embodiments, the concentration is from $1 \times 10^{-4}$ M to $4 \times 10^{-2}$ M, from $2 \times 10^{-3}$ M to $1.2 \times 10^{-2}$ M and from $4 \times 10^{-3}$ M to $1 \times 10^{-2}$ M. In embodiments, the concentration of carbonylation catalyst in the reaction medium may be at least 7.5 millimolar (mmol) or may be in a range of 1 mmol to 100 mmol, or 2 mmol to 5 mmol, or 2 mmol to 75 mmol, or 5 mmol to 50 mmol, or 7.5 mmol to 25 mmol of catalyst per liter of reaction medium. While these concentrations are sufficient to cause carbonylation to proceed, higher concentrations may be used so long as such higher concentrations do not cause an unsatisfactory extent of byproducts.

In embodiments, the present disclosure relates to reactor streams or reactor effluents of a carbonylation process that is conducted in liquid phase or in gas phase. In embodiments, the carbonylation reaction contains one or more liquid components that may be selected from acetic acid, methanol, water, organic iodide (e.g., methyl iodide), methyl acetate, or combinations thereof.

The reaction medium may include an alkyl acetate, such as methyl acetate, for example. The concentration of alkyl acetate in the reaction medium may be in a range of from 0.6 wt % to 36 wt %, from 2 wt % to 20 wt %, from 2 wt % to 16 wt %, from 3 wt % to 10 wt %, or from 2 wt % to 8 wt %, based on the total reaction medium weight. In embodiments, methyl acetate is formed in situ via esterification of methanol feed. In other embodiments methyl acetate is charged to the reactor as a co-feed along with methanol where methyl acetate may vary from 0% to 100% of the total feed. Those skilled in the art will appreciate that the steady state methyl acetate concentration in the reactor is a function of reactor conditions and is largely unrelated to its source (in situ generated or added in feed). In embodiments, methyl acetate concentration is maintained to produce a mass ratio between methyl acetate and the rhodium catalyst from 1000:1 to 2:1, such as a ratio from 700:1 to 5:1 and from 275:1 to 14:1.

In embodiments, the reaction medium further includes one or more promoters. For example, the reaction medium may include an iodide promoter. The iodide promoter is an organic iodide such as methyl iodide. The concentration of such promoters in the reaction medium may be in a range of from 0.6 wt % to 36 wt %, from 4 wt % to 24 wt %, or from 6 wt % to 20 wt %, based on the total weight of the reaction medium. The iodide promoter may be introduced to the reaction medium in a form such that the introduced compound will directly promote the carbonylation reaction (e.g., introduction of methyl iodide to the carbonylation reaction). Alternatively, one or more compounds may be introduced to the reaction medium to form in-situ generated compounds capable of promoting the carbonylation reaction. For example, a carbonylation process may comprise introduction of hydrogen iodide to the reaction medium to form methyl iodide therefrom, which acts as a promoter. Thus, in embodiments, the reactor effluent or carbonylation product is produced from a carbonylation process which comprises a liquid medium and comprises an iodide source. In embodiments, the iodide source is methyl iodide or hydroiodic acid. In embodiments, the methyl iodide is added directly to the reaction mixture. In embodiments, the methyl iodide can be generated in situ from the reaction of hydroiodic acid with methanol. Without being bound by theory, it is believed that the methyl iodide oxidatively adds to the rhodium catalyst as the first step of the catalytic cycle.

A variety of different concentrations of the iodide source may be used in the carbonylation reaction of the present disclosure. In embodiments, the amount of methyl iodide added to the reaction comprises a concentration from 0.6 wt % to 36 wt % of the liquid reaction component, such as from 3.6 wt % to 24 wt % of the liquid reaction component. The amount of methyl iodide can also be determined as a molarity of the liquid reaction component. In embodiments, the concentration of methyl iodide is from 0.05 M to 3.0 M, including from 0.3 M to 2.0 M. In embodiments, hydroiodic acid is used as the iodide source. In embodiments, hydrogen iodide (HI) is used as the iodide source. In embodiments, the concentration of hydroiodic acid or hydrogen iodide used in the carbonylation reaction is from 0.6 wt % to 23 wt %, including from 2.3 wt % to 11.6 wt %. The concentration of the hydroiodic acid or hydrogen iodide can be measured as the molarity of the liquid reaction component. In embodiments, the concentration of hydroiodic acid or hydrogen iodide is from 0.05 M to 2.0 M, such as from 0.2 M to 1.0 M.

In embodiments, the carbonylation reaction further comprises adding a carboxylic acid to the liquid reaction component. In embodiments, the carboxylic acid is acetic acid. In embodiments, the concentration of acetic acid added to the liquid reaction component is in a range of from 20 wt % to 80 wt % or when measured in molarity from 3.0 M to 12.0 M, such as from 35 wt % to 65 wt % or when measured in molarity from 5 M to 10 M. In embodiments, the balance of the liquid reaction component is acetic acid.

In embodiments, the carbonylation catalyst is utilized with a co-catalyst. In such aspects, the carbonylation reaction can further comprise adding a second metal compound to the reaction mixture. In embodiments, the second metal is a transition metal or a post-transition metal. The co-catalyst may be selected from metals and metal compounds including osmium, rhenium, ruthenium, cadmium, mercury, zinc, gallium, indium, tungsten, or combinations thereof. In embodiments, the metal compounds include metal acetates. In embodiments, the carbonylation reaction further comprises adding one or more compounds or complexes of a metal selected from ruthenium, rhenium, osmium, cadmium, zinc, mercury, gallium, indium, or tungsten or combinations thereof. In embodiments, any soluble or heterogeneous source of ruthenium can be added to the reaction mixture to enhance the yield and production of the carbonylation process. Some non-limiting examples of ruthenium compounds or complexes that can be used in the carbonylation reaction include ruthenium halides, ruthenium carbonyl, ruthenium oxides, ruthenium carboxylates, ruthenium carbonyl complexes, organoruthenium complexes such as tetrachlorobis(benzene)diruthenium(II), dichloro(cycloocta-1,5-diene) ruthenium(II) polymer, or tetrachlorobis(4-cumene)diruthenium(II) or mixed ruthenium halocarbonyls compounds such as dichlorotricarbonylruthenium(III) dimers or dibromotricarbonyl-ruthenium(II) dimers.

In embodiments, the concentration of the second metal added to the liquid reaction component is added relative to the carbonylation catalyst. In embodiments, the amount of the second metal relative to the carbonylation catalyst is from 0.1:1 to 20:1, including from 0.5:1 to 10:1 and from 2:1 to 10:1. In embodiments, the second metal is added to the reaction medium at a concentration up to the limit of solubility of the second metal in the reaction mixture. In embodiments, the concentration of the second metal is less than 8000 ppm, including 400 ppm to 7000 ppm. In embodiments, the concentration of co-catalyst in the reaction medium may be in a range of from 500 ppm to 3000 ppm, or from 1000 ppm to 2000 ppm, based on the total reaction medium weight.

In embodiments, the carbonylation process further comprises water in the reaction mixture. In embodiments, the water is added deliberately to the reaction mixture. In embodiments, the water is a contaminant from the addition of other components. Without being bound by theory, the addition of water may promote the final conversion of the carbonylated compound into the appropriate carboxylic acid from the acid halide. In embodiments, the reaction medium thus further includes water. Based on the total weight of the reaction medium, the concentration of water in the reaction medium may be in a range of from 1 wt % to 14 wt %, from 1 wt % to 5 wt %, or from 4 wt % to 8 wt %, or less than or equal to 10 wt %, 8 wt %, or 6 wt %. The amount of water added to the reaction may be at a concentration from 4 wt % to 12 wt % relative to the total weight of the reaction mixture or in terms of molarity the amount of water may be from 2.5 M to 7.5 M, including from 4 wt % to 11 wt % or 2.5 M to 7.0 M and from 4.4 wt % to 9 wt % or 2.7 M to 6.0 M. The amount of water can, in embodiments, be measured relative to the amount of catalyst used in the reaction. In embodiments, the mass ratio of water to catalyst is from 0.5:1 to 4000:1, such as from 270:1 to 1750:1.

It is contemplated that a supplemental gas such as hydrogen may be supplied to the reaction medium. In embodiments, one of the gases added to the reaction mixture is hydrogen gas. Supplemental hydrogen may be supplied to the reaction medium to provide a total hydrogen concentration in the gaseous component of the feedstock to the carbonylation reaction in a range of from 0.1 mole percent (mol %) to 5 mol %, or from 0.3 mol % to 3 mol %. Without being bound by theory, the addition of hydrogen to the reaction mixture, particularly a reaction mixture comprising a rhodium catalyst, may decrease the selectivity of the carbonylation process favoring the production of byproducts such as aldehydes and alcohols. Furthermore, without being bound by theory, the carbonylation reactions which comprise hydrogen may exhibit increased catalytic efficacy. The amount of hydrogen gas utilized depends on the catalyst and other reactive metal components employed, as well as the identification of the desired products. In embodiments, the molar ratio of hydrogen relative to carbon monoxide (CO) in the reaction mixture is from 2:1 to 1:8, such as from 1:1 to 1:4. In embodiments, the concentration of the hydrogen added to the reaction mixture is from 0.1 mol % to 5 mol % based upon the amount of CO added to the reactor. In embodiments, the concentration of hydrogen is from 0.5 mol % to 3 mol %. In embodiments, the hydrogen gas is added to the reactor as a separate stream from the other gaseous components. In embodiments, the hydrogen gas is added as a mixture with CO. In embodiments, hydrogen gas can be added to the reaction mixture as needed in order to maintain a consistent concentration of hydrogen gas in the reaction mixture. As CO is consumed in the reaction, in embodiments, the molar ratio of hydrogen to CO can increase to a concentration from 1000:1 to 100:1. As the molar ratio of hydrogen to CO changes, in embodiments, more CO is added to the reaction mixture to increase the molar ratio of CO to hydrogen.

In embodiments, the carbonylation reaction comprises adding CO to the reaction mixture. In embodiments, the CO can be added as a gas. In embodiments, the CO is generated in situ from the ligands of one or more of the metal catalysts. In embodiments, CO is added at a pressure from 70 kPa to 5,600 kPa. In embodiments, CO is added at a pressure from 325 kPa to 3,500 kPa. In embodiments, CO is added at a pressure from 650 kPa to 2,100 kPa. In embodiments, the reaction comprises continuous addition of CO to the reaction mixture to maintain a constant molar ratio of CO as the CO is consumed in the reaction.

In embodiments, the present disclosure provides a carbonylation process which can be carried out using a wide variety of different reactor systems. In embodiments, the carbonylation process is carried out in a batch mode reactor. In embodiments, the carbonylation process is carried out in a continuous mode reactor. In embodiments, the carbonylation process is carried out in a fixed bed or fluidization reactor.

In embodiments, the carbonylation method of the present disclosure is conducted under an increased pressure. In embodiments, the reaction pressure is from 1350 kPa to 8,500 kPa, such as from 2,000 kPa to 4,200 kPa or 2,800 kPa. In embodiments the temperature of the carbonylation reaction is elevated above room temperature. In embodiments, the temperature of the carbonylation reaction is greater than 100° C., such as from 150° C. to 225° C., from 160° C. to 220° C., from 170° C. to 200° C. or 175° C.

The reaction effluent of the carbonylation process can include the use of a phosphine oxide in production of a carboxylic acid in an amount relative to the rhodium catalyst. It is contemplated that any amount of phosphine oxide may be used in the reaction process. In embodiments, the amount of phosphine oxide used is sufficient to stabilize the rhodium carbonylation catalyst, such as greater than 50 equivalents per equivalent of rhodium catalyst or greater than 100 equivalents per equivalent of rhodium catalyst. The amount of phosphine oxide used can also be described in terms of a concentration of the reaction mixture. In embodiments, the amount of phosphine oxide used is from 0.03 M to 2.25 M, such as from 0.4 M to 1.4 M. In embodiments, the concentration of the phosphine oxide is sufficient to achieve an improvement in some process metric such as increased rate, increased yield, or decreased production of one or more byproducts. Without being bound by theory, the addition of phosphine oxide may prevent the precipitation of the active rhodium catalyst and thus maintain the rate of the carbonylation reaction.

In embodiments, the carbonylation further comprises the addition of an iodide salt. It is contemplated that the iodide anion of the salt may be the relevant element for the carbonylation reaction and, as such, the identity of the cation may be less relevant. Thus, in embodiments, an iodide salt with any cation may be used in the carbonylation reaction described herein. In embodiments, the iodide salt is a metal iodide salt. In embodiments, the metal is a Group 1, Group 2, or transition metal cation. In embodiments, the metal is a Group 1 or Group 2 metal cation. In embodiments, the metal is an alkali metal cation. In embodiments, the iodide salt is an organic cation iodide. In embodiments, the organic cation is a quaternary organic cation. In embodiments, the quaternary organic cation comprises a positively charged quaternary nitrogen atom. The concentration of iodide salt which may be used in the carbonylation method varies widely and is dependent on the concentration of the reactive component. Without being bound by theory, the ratio of iodide salt to methyl acetate, methanol, dimethyl ether, or other reactive intermediates used within the carbonylation reaction affects the reaction rate. In embodiments, the concentration of the iodide salt is from 1 wt % to 30 wt % or from 0.075 M to 2.25 M, from 2 wt % to 20 wt % or from 0.075 M to 1.5 M or from 10 wt % to 20 wt % or from 0.75 M to 1.5 M. In embodiments, the molar ratio of the metal to the rhodium catalyst is greater than 38:1 or greater than 75:1. In embodiments, a molar ratio of the metal to the rhodium catalyst is sufficient to stabilize the rhodium catalyst.

In embodiments, the reaction conditions comprise using a low concentration of a metal iodide, such as less than or equal to 5, 4, 3, 2, or 0 wt %. In embodiments, the carbonylation is performed in the absence of a metal iodide. For example, in embodiments, the carbonylation is performed in the absence of a lithium source, such as lithium iodide, such that streams throughout (including, without limitation, the vapor fraction in vapor stream 126, the side drawn acetic acid process stream 136, the dried acetic acid process stream 141, the acetic acid process stream 156 withdrawn from heavy ends column 150, the aqueous intermediate stream introduced into adsorbent vessel 210 via, for example, stream 138b', 139a, 139b', 142a, or a combination thereof, as described in detail hereinbelow) comprise less than or equal to 1, 5, or 50 ppm lithium. In embodiments, when a co-catalyst or promoter is added to the reaction, the concentration of the metal iodide is less than 3.5 wt %, including less than 3.0 wt %, less than 2.5 wt %, less than 2.0 wt % and less than 1.5 wt %. In embodiments, the concentration of metal iodide correlates to the total concentration of iodide in the reactor. In embodiments, the concentration of iodide in the reactor comprises iodide from the metal catalyst, metal co-catalysts or promoters, or the addition of a metal iodide. In embodiments, the concentration of iodide is measured by titrating of $AgNO_3$ into a sample of the reaction media and measuring the amount of silver iodide that precipitates from the solution.

In practice, carbonylation reaction conditions vary depending upon reaction parameters, reactor size and charge and the individual components employed. However, in embodiments, the carbonylation process may be a batch or continuous process and the carbonylation conditions may include a carbonylation pressure in a range of from 200 pounds per square inch gauge (psig) (1379 kilopascals (kPa)) to 2000 psig (13790 kPa), from 200 psig (1379 kPa) to 1000 psig (6895 kPa), or from 300 psig (2068 kPa) to 500 psig (3447 kPa), and/or a carbonylation temperature in a range of from 150° C. to 250° C., from 170° C. to 220° C., or from 150° C. to 200° C.

The carbonylation product includes the formed acetic acid. In addition to the acetic acid, the carbonylation product may include one or more impurities. Impurities are defined herein as any component in a process stream other than the targeted product itself (e.g., acetic acid is the targeted product in the carbonylation product stream). For example, the impurities present in the carbonylation product stream may include water, propionic acid, aldehydes (e.g., acetaldehyde, crotonaldehyde, butyraldehyde and derivatives thereof), alkanes, formic acid, methyl formate, or combinations thereof, as well as additional compounds other than the acetic acid, depending on the specific process. As noted above and described in more detail hereinbelow, oxidizable impurities in various aqueous intermediate streams can be removed via the system and method of this disclosure.

In one or more embodiments, components within the carbonylation product stream (or at least a portion thereof) may be separated from one another via flash separation into a liquid fraction and a vapor fraction. The liquid fraction may include residual carbonylation catalyst as well as other components, while the vapor fraction may include acetic acid, unreacted reactants, water, methyl iodide and impurities generated during the carbonylation reaction. For example, the vapor fraction may include acetic acid, water, methanol, methyl acetate, methyl iodide, acetaldehyde, or a combination thereof. The liquid fraction may be recycled to the carbonylation reaction while the vapor fraction may undergo supplemental separation, for example, as described hereinbelow.

For example, in the embodiment of FIG. 1, flash vessel 120 may be configured to receive carbonylation reaction product stream 111 from reactor 110. In flash vessel 120, stream 111 may be separated into a vapor stream 126 and a liquid stream 121. Vapor stream 126 may be communicated to a light-ends column 130, and liquid stream 121 may be communicated to reactor 110. In embodiments, vapor stream 126 may comprise acetic acid, water, methyl iodide, methyl acetate, HI, or a combination thereof, for example.

Flash vessel 120 may be operated at a pressure below that of reactor 110. In embodiments, flash vessel 120 may be operated at a pressure of from 10 psig to 100 psig. In embodiments, flash vessel 120 may be operated at a temperature of from 100° C. to 160° C.

Impurities are often separated from the acetic acid prior to use thereof in subsequent processes, such as industrial processes. Such separation processes may include those available in the relevant literature and may include separating one or more of the impurities from the acetic acid within a process stream (wherein the process stream may be referred to as "impure acetic acid") to form a more pure acetic acid. Such separation processes may be performed, for example via one or more methods including, but not limited to, extraction, distillation, extractive distillation, caustic treatment, scavenging, adsorption, or a combination thereof. Such separation processes can be utilized to provide, from the vapor stream 126, an acetic acid product and an aqueous intermediate stream treated via contact with an adsorbent as per this disclosure to reduce the amount of oxidizable impurities therein. As used herein, the term "more pure acetic acid" refers to an acetic acid stream having a concentration of one or more impurities that is reduced in comparison to the concentration of that impurity in an upstream feed stream. It is to be noted that use of the term "acetic acid process stream" herein refers to any stream containing the product acetic acid.

The supplemental separation may include a first distillation column (e.g., a light ends distillation column) adapted to separate components of the vapor fraction and form a first distillation column overhead stream (also referred to as a light ends overhead stream), an acetic acid stream, and a first distillation column bottoms stream (also referred to as a light ends bottoms stream). The acetic acid stream may comprise primarily acetic acid and water, and may be extracted as a side draw from light ends distillation column 130, in embodiments. The light ends overhead stream may comprise methyl iodide, water, methanol, methyl acetate, impurities or combinations thereof. For example, the light ends overhead can comprise methyl iodide, water, methyl acetate, acetic acid, acetaldehyde, or a combination thereof.

In the embodiment of FIG. 1, light-ends distillation column 130 may include a distillation column and equipment associated with the distillation column including but not limited to a heat exchanger, a decanter 134, pumps, compressors, valves, and other related equipment. Light-ends column 130 may be configured to receive vapor stream 126 from flash vessel 120. First or light-ends overhead stream 132 includes overhead product from light-ends column 130, and light-ends bottoms stream 131 includes bottoms product from light-ends column 130. Light-ends bottoms stream 131 may recycle light ends bottoms to flash vessel 120, in embodiments. Stream 136 may extract acetic acid product (e.g., as a side draw) from light-ends column 130. Other streams may be included, for example, a stream that may recycle a bottoms mixture of light-ends column 130 back into the light-ends column 130. Any stream received by or emitted from the light-ends column 130 may pass through a pump, compressor, heat exchanger, and the like as is common in the relevant art. Light-ends column 130 may include a decanter 134, and light-ends overhead stream 132 may pass into decanter 134.

In embodiments, light-ends column 130 may comprise at least 10 theoretical stages or 16 actual stages. In embodiments, light-ends column 130 may comprise at least 14 theoretical stages. In embodiments, light-ends column 130 may comprise at least 18 theoretical stages. In embodiments, one actual stage may equal approximately 0.6 theoretical stages. Actual stages can be trays or packing. The reaction mixture may be fed via stream 126 to light-ends column 130 at the bottom or the first stage of light-ends column 130.

Light-ends overhead stream 132 may include acetaldehyde, water, carbon monoxide, carbon dioxide, methyl iodide, methyl acetate, methanol and acetic acid, or a combination thereof. Light-ends bottoms stream 131 may include acetic acid, methyl iodide, methyl acetate, HI, water, or a combination thereof. Acetic acid process stream 136 may include acetic acid, HI, water, heavy impurities, or a combination thereof.

In embodiments, light-ends column 130 may be operated at an overhead pressure within the range of 20 psia (1.4 kg/cm$^2$) to 50 psia (3.5 kg/cm$^2$), alternatively, the overhead pressure may be within the range of 30 psia (2 kg/cm$^2$) to 35 psia (2.5 kg/cm$^2$). In embodiments, light-ends column 130 may be operated at an overhead temperature within the range of 95° C. to 150° C., alternatively, the overhead temperature may be within the range of 110° C. to 150° C., alternatively, the overhead temperature may be within the range of 125° C. to 150° C. In embodiments, light-ends column 130 may be operated at a bottom pressure within the range of 25 psia (1.8 kg/cm$^2$) to 45 psia (3.2 kg/cm$^2$), alternatively, the bottom pressure may be within the range of 30 psia (2.1 kg/cm$^2$) to 50 psia (3.5 kg/cm$^2$). In embodiments, light-ends column 130 may be operated at a bottom temperature within the range of 115° C. to 170° C., alternatively, the bottom temperature is within the range of 125° C. to 150° C. In embodiments, acetic acid process stream 136 may be emitted from light-ends column 130 as a liquid side draw. Stream 136 may be operated at a pressure within the range of 25 psia (1.8 kg/cm$^2$) to 45 psia (3.2 kg/cm$^2$), alternatively, the pressure may be within the range of 30 psia (2.1 kg/cm$^2$) to 50 psia (3.5 kg/cm$^2$). In embodiments, the temperature of stream 136 may be within the range of 90° C. to 140° C., alternatively, the temperature may be within the range of 125° C. to 135° C. Stream 136 may be taken between the fifth to the eighth actual stage of light-ends column 130.

The first overhead stream may be condensed and separated in a decanter to form, relative to each phase, a "light" aqueous phase and a "heavy" organic phase. In the embodiment of FIG. 1, decanter 134 is configured for the separation of a light aqueous phase extracted therefrom via light aqueous phase decanter outlet stream 139 from a heavy organic phase extracted therefrom via heavy organic phase decanter outlet stream 138. The heavy, organic phase in heavy organic phase decanter outlet stream 138 may comprise acetaldehyde, methyl iodide (MeI), methyl acetate, hydrocarbons, acetic acid, water, or a combination thereof. In embodiments, stream 138 may be essentially non-aqueous with a water concentration of less than 1 wt %. In embodiments, stream 138 may comprise MeI greater than 50% by weight of the stream. In embodiments, the heavy organic phase comprises methyl iodide and oxidizable impurities. For example, the heavy organic phase can comprise from 0.1 to 5, from 0.2 to 4, or from 0.5 to 2 weight percent oxidizable impurities. The light, aqueous phase stream 139 may comprise water (e.g., greater than 50% by weight of the stream), acetic acid, methyl acetate, methyl iodide, oxidizable impurities, or a combination thereof. For example, the light aqueous phase can comprise from 0.1 to 5, from 0.2 to 4, or from 0.5 to 2 weight percent oxidizable impurities. Make-up water may be introduced into decanter 134 via stream 133.

Portion(s) of the light aqueous phase stream 139 may be recycled to reactor 110 via line 112 or for further light ends distillation in light-ends distillation column 130 via stream 135. Stream 135 may thus recycle a portion of the light aqueous phase in stream 139 from decanter 134 back to light-ends column 130. Stream 139 may recycle a portion of the light aqueous phase of decanter 134 back to reactor 110 via, for example, stream 112. Stream 138 may emit from decanter 134 and may recycle at least a portion of the heavy organic phase back to reactor 110 via, for example, stream 112 or be may combined with any of the other streams that feed the reactor.

According to this disclosure, at least a portion of the light aqueous phase stream 139, is introduced, via light aqueous phase stream 139a, into adsorbent vessel 210 for the removal of oxidizable impurities therefrom. An oxidizable impurity-reduced stream may be returned to the process from adsorbent vessel 210 via line 139b.

In embodiments, at least a portion the light aqueous phase, at least a portion of the heavy organic phase, or a combination thereof is subjected to further distillation and/or extraction (e.g., water extraction) to increase the aqueous content and/or concentrate the oxidizable impurities prior to introduction into adsorbent vessel 210, prior to recycle to reactor 110 (for example, via streams 138 and/or 139) and/or to light-ends column 130 (for example, via stream 135), or a combination thereof. For example, the aqueous content and/or concentration of the oxidizable impurities may be increased in the entirety of the heavy organic phase extracted from decanter 134 or some fraction thereof (e.g., in stream 138 and/or 138a) and/or in the entirety of the light aqueous phase extracted from decanter 134 or some fraction thereof (e.g., in stream 135, 139, and/or 139a) via one or more stages of distillation, extraction, or both.

In the embodiment of FIG. 1, all or a portion of light aqueous stream 139/139a can be introduced to distillation/extraction apparatus 160 via stream 139a' for the removal of impurities therefrom via one or more stages of distillation, extraction, or both, prior to introduction of an aqueous intermediate stream having concentrated oxidizable impurities into adsorbent vessel 210 via line 139b'. In the embodiment of FIG. 1, all or a portion of heavy organic stream 138/138a can be introduced to distillation/extraction apparatus 160 via stream 138a' for the removal of impurities therefrom via one or more stages of distillation, extraction, or both, prior to introduction of an aqueous intermediate stream having concentrated oxidizable impurities into adsorbent vessel 210 via line 138b'. In other embodiments, not shown in FIG. 1, the entirety of the light aqueous phase and/or the heavy organic phase removed from decanter 134 is subjected to one or more stages of distillation, extraction, or both prior to introduction of an aqueous stream produced via the one or more stages of distillation, extraction, or both into adsorbent vessel 210 via line 138b' or 139b'. In embodiments, a stream 139c resulting from treatment of all or a portion of the light aqueous phase 139 in apparatus 160 can be recycled to reactor 110 (for example, via streams 139b and/or 139) and/or to light-ends column 130 (for example, via streams 139b, 139, and/or 135). In embodiments, a stream 138c resulting from treatment of all or a portion of the heavy organic phase 138 in apparatus 160 can be recycled to reactor 110 (for example, via streams 138b and/or 138).

Although indicated as a single vessel 160 in the embodiment of FIG. 1, a carboxylation system 100 may comprise a separate distillation/extraction apparatus 160 for treating portions of the light aqueous phase and the heavy organic phase from decanter 134, and each distillation/extraction apparatus 160 can comprise multiple distillation columns and/or multiple extractors (e.g., multiple water extraction units) that may be operated in any suitable order and manner known to those of skill in the art.

For example, impurities may be removed from the heavy organic phase extracted from decanter 134 by contact within distillation/extraction apparatus 160 with a silicoaluminophosphate (SAPO) as described in U.S. Patent App. No. 2017/0158592, and/or 2017/0158596; impurities may be removed from the heavy organic phase extracted from decanter 134 by contact within distillation/extraction apparatus 160 with a resin or a liquid methanesulfonic acid (MSA) catalyst, as described in U.S. Pat. No. 8,969,613; impurities may be removed from the light aqueous phase and the heavy organic phase from decanter 134 via distillation and extraction within distillation/extraction apparatus 160 as described in U.S. Pat. No. 8,940,932; impurities may be removed from the light aqueous phase extracted from decanter 134 by various combinations of distillation and extraction thereof within a distillation/extraction apparatus 160, as described in U.S. Pat. Nos. 7,223,886; 9,056,825; and/or 9,216,936. The disclosure of each of the aforementioned patents and patent applications are hereby incorporated herein by reference for purposes not contrary to this disclosure.

In embodiments, an aqueous stream 139b' produced during extraction and/or distillation of light aqueous phase 139a' in distillation/extraction apparatus 160 and introduced into adsorbent vessel 210 (i.e., as an aqueous intermediate stream) comprises from 0.05 to 50, from 0.1 to 50, or from 0.5 to 50 weight percent oxidizable impurities. In embodiments, an aqueous stream 139b' produced during extraction and/or distillation of light aqueous phase 139a' in distillation/extraction apparatus 160 and introduced into adsorbent vessel 210 (i.e., as an aqueous intermediate stream) comprises from 10 to 90, from 15 to 90, or from 10 to 85 weight percent water. In embodiments, an aqueous stream 139b' produced during extraction and/or distillation of light aqueous phase 139a' in distillation/extraction apparatus 160 and introduced into adsorbent vessel 210 (i.e., as an aqueous intermediate stream) comprises less than or equal to 70, 60, 50, 40, 30, 20, or 10 weight percent acetic acid.

In embodiments, an aqueous stream 138b' produced during extraction and/or distillation of heavy organic phase 138a' in a distillation/extraction apparatus 160 and introduced into adsorbent vessel 210 (i.e., as an aqueous intermediate stream) comprises from 0.05 to 50, from 0.1 to 50, or from 0.5 to 50 weight percent oxidizable impurities. In embodiments, an aqueous stream 138b' produced during extraction and/or distillation of heavy organic phase 138a' in a distillation/extraction apparatus 160 and introduced into adsorbent vessel 210 (i.e., as an aqueous intermediate stream) comprises from 10 to 90, from 15 to 90, or from 10 to 85 weight percent water. In embodiments, an aqueous stream 138b' produced during extraction and/or distillation of heavy organic phase 138a' in distillation/extraction apparatus 160 and introduced into adsorbent vessel 210 (i.e., as an aqueous intermediate stream) comprises less than or equal to 70, 60, 50, 40, 30, 20, or 10 weight percent acetic acid.

The acetic acid process stream 136 may be passed to a drying column, as described further hereinbelow, to remove any water contained therein. The drying column may comprise a vessel and equipment associated with the vessel including but not limited to heat exchangers, decanters, pumps, compressors, valves, and the like. In the embodiment of FIG. 1, carbonylation system 100 comprises drying column 140 configured to receive acetic acid process stream 136 from light-ends column 130 and remove water therefrom. Drying column 140 may separate components of stream 136 into drying column water stream 142 and dried acetic acid process stream 141.

Stream 142, comprising drying column water, may emit from drying column 140, recycle back to drying column 140 via stream 145, and/or recycle back to reactor 110 via stream 148 (via, for example, stream 112). A portion of the drying column water stream 142a can be introduced, in embodiments, into adsorbent vessel 210. In embodiments, an impurity-reduced stream 142b produced via introduction of drying water stream 142 or a derivative thereof (e.g., drying water stream 142a) is returned via line 148 to reactor 110, and/or via line 142b and 145 into drying column 140. Thus, as noted herein, a variety of aqueous intermediate streams may be passed through adsorbent vessel 210.

In embodiments, drying column water stream 142/145/148/142a can comprise greater than or equal to 80, 40, or 10 wt % water, less than or equal to 10, 40, or 80 wt % acetic acid, from 0.01 to 5 wt %, from 0.05 to 5 wt %, or from 0.1 to 5 wt % oxidizable impurities, greater than or equal to 0.1, 0.1, or 0.5 wt % oxidizable impurities, or less than or equal to 5, 2, or 1 wt % oxidizable impurities.

Stream 141 may emit from the drying column 140 and may include de-watered or 'dried' acetic acid product. In embodiments, the side draw acetic acid process stream 136 comprises greater than or equal to 2, 5, or 10 wt % water, and the dried acetic acid process stream 141 can comprise less than or equal to 5000, 1000, or 500 ppm water. Dried acetic acid process stream 141 can further comprise from 99.5 to 99.9, from 99.6 to 99.9, or from 99.7 to 99.9 wt % acetic acid or greater than or equal to 99.5, 99.6, or 99.7 wt % acetic acid, from 10 to 2000, from 10 to 10000, or from 15 to 2000 ppm oxidizable impurities, greater than or equal to 10, 50, or 100 ppm oxidizable impurities, or less than or equal to 2000, 1000, or 10 ppm oxidizable impurities. In embodiments, at least a portion of dried acetic acid process stream 141 is subjected to acidic ion exchange for the removal of oxidizable impurities therefrom.

Stream 142 may pass through equipment that is readily available, for example, a heat exchanger or separation vessel before streams 145 or 148 recycle components of stream 142 to drying column 140 or reactor 110, respectively, or stream 142a introduces drying column water to adsorbent vessel 160. Other streams may be included, for example, a stream may recycle a bottoms mixture of drying column 140 back into drying column 140. Any stream received by or emitted from drying column 140 may pass through a pump, compressor, heat exchanger, separation vessel, and the like as is common in the art.

While many processes exist for the separation of the impurities from product carboxylic acid streams, such processes can be difficult to implement, are not effective, and/or are costly. Thus, continuous efforts have been underway to improve and develop methods to separate these impurities from acetic acid. According to this disclosure, adsorption with specific adsorbents as described hereinbelow is employed to effect separation of one or more oxidizable impurities from an aqueous intermediate stream comprising weight percent levels of oxidizable impurities and substantial (e.g., greater than or equal to 30, 40, 50, 60, 70, 80, or 85 wt %) water. As noted hereinabove, any carbonylation system and method can be utilized to provide the aqueous, impurity-containing, intermediate stream treated according to this disclosure. Any stream (or portion thereof) containing suitable levels of target impurities (e.g., oxidizable impurities/PRCs) and/or water as noted herein may contact the adsorbent vessel to reduce such oxidizable impurities. However, one or more embodiments include contacting a drying column water stream (such as drying column water stream 142a) with the adsorbent; contacting an aqueously extracted (and/or distilled) decanter heavy organic phase stream (such as an aqueous stream 138b' produced via aqueous extraction of heavy organic phase 138a' or aqueous extraction of an overhead produced via distillation of heavy organic phase 138a'), which can consist essentially of water and impurities, with the adsorbent; contacting an aqueously extracted (and/or distilled) decanter light aqueous phase stream (such as an aqueous stream 139b' produced via aqueous extraction of light aqueous phase 139a' or a distilled portion of light aqueous phase 139a') with the adsorbent; contacting at least a portion of the light aqueous phase extracted from decanter 134 (or a distilled and/or aqueously extracted portion thereof, as noted previously) with the adsorbent; or a combination thereof.

Although described with reference to the carboxylic acid production system of FIG. 1, it is to be understood that an aqueous intermediate stream purified via contact with an adsorbent according to this disclosure can be the product of a variety of systems and methods operable to provide such an aqueous (e.g., greater than or equal to 30 wt % water), oxidizable impurity-containing (e.g., wt % level of oxidizable impurities, greater than or equal to 0.5 wt % oxidizable impurities) aqueous intermediate stream. For example, alternative embodiments for a carboxylic acid production system 100 whereby such an aqueous intermediate stream suitable for treatment according to this disclosure can be obtained may be found in U.S. Pat. Nos. 6,552,221; 7,223,886; 7,683,212; 8,940,932; 8,969,613; 9,056,825; 9,216,936; U.S. Patents Pub. No. 2016/0289153; 2016/0376213; 2017/0158592; 2017/0158596; the disclosure of each of which is hereby incorporated herein by reference for purposes not contrary to this disclosure.

Adsorbent vessel 210 comprises an adsorbent. In embodiments, the adsorbent comprises a zeolite, an acidic ion exchange resin, a silicate, or a combination thereof.

In embodiments, the adsorbent has a silica to alumina (Si/Al) molar ratio in a range of from 1/1 to 400/1, from 10/1 to 400/1, from 20/1 to 400/1, or greater than or equal to 20/1, 30/1, 40/1, 50/1, 60/1, 70/1, 80/1, 90/1, 100/1, 200/1, 300/1, or 400/1. A higher Si/Al molar ratio may provide for enhanced removal of oxidizable impurities.

In embodiments, the surface area of the adsorbent promotes the interaction of the oxidizable impurities therewith. In embodiments, the adsorbent has a surface area of greater than or equal to 200, 300, or 350 $m^2/g$, or more, less than or equal to 500, 400, or 300 $m^2/g$, or a combination thereof. In embodiments, the adsorbent has an average particle size of less than or equal to 50, 40, 30, 20, 10, 5, or 2 micrometers (μm).

In embodiments, the adsorbent comprises a zeolite. The zeolite can comprise a nanozeolite, an H—Y zeolite (Y zeolite in H+ form), or a combination thereof. In embodiments, the zeolite comprises a nanozeolite, which as utilized herein refers to a zeolite having an average particle size, as determined by techniques such as light scattering and laser diffraction, of less than or equal to 300, 250, or 200 nm. Suitable zeolites include ZSM-22, ZSM-5-38, Nano ZSM-5, Z—HY zeolite, or a combination thereof.

In embodiments, the adsorbent comprises a silicate. Suitable silicates include, for example, MCM-22, MCM-41, or a combination thereof.

In embodiments, the adsorbent comprises an acidic ion exchange resin. A wide variety of ion exchange resins may be used to remove oxidizable impurities from the aqueous intermediate stream according to this disclosure. One type of ion exchange resin which may be used comprises macroreticular polymeric resins. Depending on the actual mechanism of removal and the amounts of impurities, other resins such as mesoporous or gel may be employed.

The acidic ion exchange resin can comprise a macroreticular polymeric ion exchange resin, including, but not limited to, strongly acidic resins which are capable of binding cationic species. In embodiments, the acidic ion exchange resin is a strongly acidic cation exchange resin. Such strongly acidic resins have acid functionalities with pKa values less than 1. For example, AMBERLYST® 15 has a sulfonic acid functionality; the pKa for para-toluene sulfonic acid is −2.8. In embodiments, the acidic ion exchange resin is macroreticular, macroporous, mesoporous, polymeric, gel, or a combination thereof. In embodiments, the resin is a polymeric resin comprising discrete particles containing cross-linked polystyrene with divinyl benzene which contain active sites. The active sites of the resin are chemical groups in the resin which bind to agents which remove impurities from the acetic acid process stream contacted therewith. In embodiments, these chemical groups are pH sensitive and protonation or deprotonation leads to the development of a charged species. In embodiments, the active sites of the resin are strongly acidic groups such as sulfonic acids or are weakly acidic groups such as carboxylic acids. In embodiments, the acidic ion exchanger 210 can be utilized with the acid form (e.g., the $H^+$-form) of the ion exchange resin.

In embodiments, the acidic ion exchange resin is selected from AMBERLITE™ IR120, AMBERLYST® 15, AMBERLYST® 15-Dry, DOWEX™ Marathon C-10 Resin, or DOWEX® DR-2030, each available from the DOW Chemical Company, PUROLITE C145, or PUROLITE CT145, each available from Purolite, or a combination thereof.

In embodiments, the acidic ion exchange resin has a minimum number of active sites from 1 equivalent to 4 equivalents per liter, as determined by ammonia adsorption or titration. In embodiments, the minimum number of active sites is from 1.5 equivalents to 3.0 equivalents per liter. In embodiments, the acidic ion exchange resin has a concentration of active sites of greater than or equal to 0.7, 1.1 or 1.5 equivalents/kg, less than or equal to 8.0, 7.0, 6.0, 5.0, 4.3 or 1.6 equivalents/kg, or a combination thereof. In embodiments, any commercially available strongly acidic ion exchange resin is used to remove oxidizable impurities from the aqueous intermediate stream being treated.

In embodiments, the acidic ion exchange resin contains a percentage of crosslinking. In embodiments, the amount of crosslinking, as determined by the extent of swelling upon water uptake, is from 1% to 25%, such as from 2% to 15% or from 4% to 12%. In embodiments, the particle size of the ion exchange resin, as determined by techniques such as light scattering and laser diffraction, has a harmonic mean size from 0.1 mm to 4 mm, including from 0.2 mm to 2 mm and from 0.5 mm to 1 mm. In embodiments, the uniformity coefficient of the acidic ion exchange resin particles is from 1.1 to 4, such as from 1.5 to 2. In embodiments, the particle size is highly uniform and contains less than 10% of particles outside the range from 0.3 mm to 1.2 mm, including less than 5% of particles outside the range from 0.3 mm to 1.2 mm. In embodiments, it is contemplated that the size of the particles changes when exposed to solvent, water, and/or the acetic acid stream being treated. In embodiments, the particles exhibit swelling from the dry state to the aqueous state of greater than 25 volume percent (vol %), including greater than 35 vol %.

In embodiments, the surface area of the ion exchange resin promotes the interaction of the acetic acid stream with the active site of the resin. In embodiments, the ion exchange resin has a surface area, as determined by BET nitrogen adsorption, of greater than or equal to 30, 40, 50, 60, 70, 80, 90 $m^2/g$, or more, less than or equal to 500, 400, 300, 200, 100, 90, 80, 70, or 60 $m^2/g$, or a combination thereof. In embodiments, the ion exchange resin has an average pore diameter, as determined by techniques such as atomic force microscopy, of greater than or equal to 10, 15, 20, 25, 30, 35, or 40 nm, less than or equal to 100, 90, 80, 75, 70, 60, or 50 nm, or a combination thereof. In embodiments, the total pore volume of the ion exchange resin is greater than or equal to 0.2, 0.3, or 0.4 mL/g, less than or equal to 0.7, 0.6, or 0.5 mL/g, or a combination thereof.

According to this disclosure at least a portion of the aqueous intermediate stream is contacted with an adsorbent, as described above, at conditions sufficient to reduce the concentration of one or more impurities present in the aqueous intermediate stream. The contacting of the at least a portion of the aqueous intermediate stream with the adsorbent may be effected in the presence of at least 30, 40, 50, 60, 70, 80, or 85 weight percent (wt %) water. In embodiments, the aqueous intermediate stream comprises at least 30, 40, 50, 60, 70, 80, or 85 wt % water, water is added such that the contacting of the aqueous intermediate stream is effected in the presence of at least 30, 40, 50, 60, 70, 80, or 85 wt % water, or a combination thereof. In embodiments, the aqueous intermediate stream contacted with the adsorbent consists almost entirely of water and impurities. Such a stream may be, for example, an aqueously extracted decanter heavy phase stream.

In embodiments, the aqueous intermediate stream contacted with the adsorbent as per this disclosure comprises greater than or equal to 0.05, 0.5, 10, or 50 wt % of one or more oxidizable compounds, based on the total weight of the aqueous intermediate stream. In embodiments, the aqueous intermediate stream contacted with the adsorbent as per this disclosure comprises water at a concentration in a range of from 30 to 95 wt %, from 40 to 90 wt %, or from 35 to 95 wt %, or greater than or equal to 30, 40, 50, 60, 70, or 85 wt % based on the total weight of aqueous intermediate stream.

At least a portion of the aqueous intermediate stream contacts the adsorbent under conditions sufficient to reduce the concentration of one or more oxidizable impurities present therein. For example, the concentration of one or more of the oxidizable impurities may be reduced by at least 10, 20, 30, 40, 50, 60, 70, or 80%. In embodiments, a concentration of oxidizable impurities in the purified product is decreased by at least 30, 40, 50, 60, 70, 80, 85, 90, 95, or 98% relative to a concentration of oxidizable impurities in the aqueous intermediate stream. In embodiments, the purified product (e.g., the impurity-reduced stream 138$b$, 139$b$, and/or 142$b$, resulting from contact with the adsorbent) comprises less than or equal to 0.01, 3 or 20 wt % oxidizable impurities, based on a total weight of the purified product. In embodiments, the purified product comprises greater than or equal to 30 to 85 wt % water, based on a total weight of the purified acetic acid product.

In embodiments, the removal of oxidizable impurities via adsorbent contact as per this disclosure provides for the production of a purified acetic acid product (e.g., in acetic acid process stream 156 or 171 that has an acetaldehyde concentration, as determined, for example, via FTIR spectroscopy as described in U.S. Pat. No. 8,969,613 (which is hereby incorporated herein by reference in its entirety for purposes not contrary to this disclosure), that passes the PT test without further purification.

At least a portion of the aqueous intermediate stream to be subjected to adsorbent contact as per this disclosure may contact the adsorbent via methods available in the relevant literature. For example, the adsorbent may be disposed as a bed in a column and the at least a portion of aqueous intermediate stream may pass through the bed to reduce the concentration of one or more components/impurities therein. The adsorbent may be disposed in the fixed bed by manners available in the relevant literature. In embodiments, the aqueous intermediate stream to be treated as per this disclosure is passed through a column of the adsorbent at a flow rate in the range of from 0.1 to 50 bed volumes per hour (BV/h), from 1 to 40 BV/h, or from 5 to 30 BV/h, wherein a flow rate of 1 BV/h means that a quantity of crude acetic acid product equal to a volume occupied by the fixed bed of adsorbent passes through the fixed bed in one hour.

The adsorbent may be loaded in the bed in an amount in a range of 1 g adsorbent per 2-15 grams of aqueous intermediate stream to be treated, or 1 g adsorbent per 5-15 grams of aqueous intermediate stream to be treated, or 1 g adsorbent per 5-10 grams of aqueous intermediate stream to be treated. In embodiments, the contacting comprises batch mode contacting in a static slurry. In embodiments, a mass ratio of the aqueous intermediate stream to be treated to the adsorbent in the slurry is in the range of from 2 to 15 grams aqueous intermediate stream to grams adsorbent, from 2 to 10 grams aqueous intermediate to grams adsorbent, or from 3 to 8 grams aqueous intermediate stream to grams adsorbent.

The conditions for contacting the adsorbent vary depending upon numerous factors, including the nature of the adsorbent, and the nature of the impurities. In embodiments, the aqueous intermediate stream to be treated is exposed to the adsorbent bed at room temperature. In embodiments, the contacting is performed at a temperature of room temperature, or less than or equal to 100° C., 90° C., 80° C., 70° C., 60° C., 50° C., 40° C. 30° C., 25° C., or 20° C. Although perhaps less efficient in terms of having to supply unnecessary thermal energy, in embodiments, the aqueous intermediate stream to be treated is exposed to the adsorbent bed at elevated temperature (i.e., above room temperature). In embodiments, the contacting is effected at a temperature(s) in a range of from room temperature to 150° C., from room temperature to 120° C., from room temperature to 100° C. As used herein, "room temperature" means that a temperature difference of a few degrees does not matter to the phenomenon under investigation. In some environments, room temperature may include a temperature in a range of 20° C. to 28° C., while in other environments, room temperature may include a temperature in a range of 10° C. to 32° C., for example. However, room temperature measurements may not include close monitoring of the temperature of the process and therefore such a recitation does not intend to bind the embodiments described herein to any predetermined temperature range.

In embodiments, a contact time of the aqueous intermediate stream to be treated with the adsorbent is less than or equal to 60, 50, 40, 30, 20, 10, 9, 8, 7, 6, 5, 4, 3, 2, or 1 minute. The contact time may comprise a time of contact for static contact, a residence time for passage of the aqueous intermediate stream to be treated through a bed of the adsorbent, or the like. As will be appreciated by one of skill in the art, an enhanced residence or contact time of the impurity-containing aqueous intermediate stream with the adsorbent may provide for enhanced impurity removal via the adsorbent. Thus, a slower flow rate through a flow-through adsorbent bed, an increased contact time for a static slurry bed of adsorbent, an increased amount of active sites per impurity level to be removed, and the like, can enhance removal of the impurities via the adsorbent.

It is contemplated that other reaction conditions and characteristics of the adsorbent affect the ability of the adsorbent to bind oxidizable impurities, which can assist in the removal of such impurities from a solution. Without undue experimentation, these reaction conditions and characteristics may be optimized by a skilled artisan.

It is contemplated that the adsorbent may occasionally undergo regeneration or replacement. The regeneration may include any regeneration procedure available in the relevant literature. The adsorbent may be regenerated either in the adsorbent bed or slurry contact vessel or may be removed from the adsorbent column or vessel for regeneration. Such regeneration is known to the skilled artisan. However, a non-limiting illustrative embodiment of in-line regeneration is described below.

In a non-limiting example of in-line regeneration, the adsorbent vessel is initially taken off-line and the adsorbent bed disposed therein is drained. The adsorbent may then undergo a regeneration step. The regeneration conditions may be any conditions that are effective for at least partially reactivating the adsorbent media. For example, regeneration may include processing the spent adsorbent at room temperature or at high temperatures and/or passing a high salt solution (e.g., 1 M NaCl) through the bed (e.g., in the opposite direction of service operation) until impurities are eluted therefrom. In embodiments, to regenerate the adsorbent, the adsorbent may be heated and the adsorbed components (e.g., crotonaldehyde) desorbed and discharged from adsorbent vessel 210. The desorbed components may be recovered or disposed as waste.

In order to minimize disruption to the process during periods of regeneration or replacement, one or more embodiments of the present disclosure utilize swing beds for the adsorption of one or more acetic acid processing impurities. In such embodiments, continuous operation can be achieved. For example, one adsorbent vessel 210 may be taken off-line for potential removal and/or regeneration of the adsorption medium therein, while the remaining adsorbent vessel 210 may remain on-line for production.

The de-watered acetic acid may be introduced into a second distillation column (e.g., a heavy-ends distillation column) adapted to separate components of the acetic acid stream and form a second or heavy ends overhead stream and a second or heavy-ends bottoms stream. The second overhead stream may include methyl iodide, methyl acetate, acetic acid, water, impurities or combinations thereof. The heavy-ends column may include a distillation column and equipment associated with the distillation column including but not limited to heat exchangers, decanters, pumps, compressors, valves, and the like.

In the embodiment of FIG. 1, heavy-ends column 150 is configured to receive de-watered acetic acid process stream 141 from drying column 140. Heavy-ends column 150 may separate components from de-watered acetic acid stream 141 into heavy-ends overhead stream 152, heavy ends bottoms stream 151, and acetic acid process stream 156. Heavy-ends overhead stream 152 and heavy-ends bottoms stream 151, comprising heavy impurities such as propionic acid, may be sent to additional processing equipment for further processing. In embodiments, stream 152 may be recycled, for example, to heavy-ends column 150. Stream 156 may comprise acetic acid product. Acetic acid process stream 156 can comprise from 99.5 to 99.9, from 99.6 to 99.9, or from 99.7 to 99.9 wt % acetic acid, greater than or equal to 99.5, 99.6, 99.7, 99.8, or 99.9 wt % acetic acid, from 100 to 5000, from 500 to 5000, or from 1000 to 5000 ppm water, less than 5000, 1000, or 500 ppm water, from 10 to 1000, from 10 to 2000, or from 100 to 1000 ppm oxidizable impurities, less than or equal to 2000, 1000, 500, 100, 50, or 10 ppm oxidizable impurities.

Acetic acid process stream 156 may be subjected to one or more additional purifications to further remove impurities (e.g., organic iodide and/or remaining oxidizable impurities) therefrom. For example, as indicated in the embodiment of FIG. 1, acetic acid process stream 156 may be introduced into one or more polishing bed 170, and a purified acetic acid product removed therefrom via acetic acid product line 171. For example, polishing bed 170 may comprise an organic iodide-removal bed wherein organic iodide can be removed from acetic acid process stream 156 to provide an organic iodide-reduced acetic acid product comprising a reduced amount of organic iodide than acetic acid process stream 156. Organic iodide removal apparatus 170 may comprise apparatus configured for treating the acetic acid process stream 156 with a resin or material comprising a metal ion, e.g., a silver loaded resin having a metal loading of greater than 15 wt % to remove inorganic or organic halides, such as described in U.S. Pat. No. 9,822,055 entitled Silver Loaded Halide Removal Resins for Treating Halide Containing Solutions, the disclosure of which is hereby incorporated herein in its entirety for purposes not contrary to this disclosure.

In embodiments, the one or more polishing bed 170 comprises an acidic ion exchanger. In such embodiments, all or a portion of the acetic acid process stream 156, all or a portion of the organic iodide-reduced acetic acid extracted from an organic iodide-removal apparatus 170, and/or all or a portion of dewatered acetic acid process stream 141 (comprising greater than or equal to 99.5, 99.7, or 99.9 wt % carboxylic acid (e.g., GAA)), and ppm levels of oxidizable impurities and less than 0.15, 0.05, or 0.02 wt % water) may be introduced into the acidic ion exchanger for the further removal of oxidizable impurities therefrom.

Features/Potential Benefits

The herein-disclosed system and method may enable the removal of oxidizable impurities from aqueous intermediate streams containing wt % levels (e.g., greater than 0.5 wt %) of oxidizable impurities/PRCs, in a simple and economical manner. Utilizing readily available and cost effective adsorbents for removal of oxidizable impurities from aqueous intermediate streams as per this disclosure can, in embodiments, enable the removal of substantial amounts of oxidizable impurities, even at room temperature.

Surprisingly, many other materials, such as silicoaluminophosphates (SAPOs), larger adsorbents (e.g., adsorbents having a particle size of greater than 10 microns), and zeolites in Na form, provide little to no removal of oxidizable impurities from such aqueous intermediate streams. In embodiments, the contact with the adsorbent according to this disclosure is performed in the presence of at least 30 wt % water.

The herein-disclosed adsorbents (e.g., nanozeolites) can be utilized to remove oxidizable impurities from a decanter light phase comprising 30 to 50 wt % water, or more. Similarly, an aqueous (PRC containing) solution resulting from distillation and aqueous extraction of a decanter light phase or a decanter heavy phase as described in the art, can be treated with an adsorbent (e.g., a nanozeolite) as per this disclosure to provide a substantially pure waste water stream. Alternatively or additionally, other process streams such as drying column reflux or 142 may be treated via adsorbent contact as per this disclosure.

The following examples merely illustrate the system and method of this disclosure. Those skilled in the art will recognize many variations that are within the spirit of this disclosure and the scope of the claims.

EXAMPLES

Example 1: Elevated Temperature Experiments

Aliquots of an 11 ppm crotonaldehyde solution in $H_2O$ were contacted with various materials in vials at 70° C. and sampled periodically to determine, by Lyondell's proprietary UV/Vis method described in U.S. Pat. No. 8,293,534, the crotonaldehyde removal (if any). The UV/Vis method for quantifying the PRC content, otherwise known as oxidizable impurity content, of an acetic acid product sample may comprise: (a) establishing a correlation between permanganate absorbances of standard samples and their PRC content by: (i) preparing two or more standard samples with known PRC contents; (ii) adding a known amount of a standard permanganate solution to each standard sample from (a)(i) to form a mixture; (iii) for each standard sample, measuring the absorbance of the mixture ($A_{mix}$) at a selected wavelength in the range of 460 to 580 nm at a set reaction time; (iv) for each standard sample, determining the permanganate absorbance ($A_{perm}$) at the set reaction time by subtracting from $A_{mix}$ the absorbance due to manganese dioxide ($A_{MnO2}$) at the selected wavelength; (v) establishing a correlation between permanganate absorbances and their PRC contents; and (b) repeating steps (a)(ii) through (a)(iv) with the unknown acetic acid sample that contains an unknown amount of PRC to determine its PRC content. In embodiments, $A_{MnO2}$ is determined by drawing a baseline across the base of a permanganate absorption band. The correlation can be a calibration curve, in embodiments. In embodiments, a solvent can be utilized to form the mixture. Such a solvent can be selected from water, alcohols, carboxylic acids, amides, nitriles, or a combination thereof. The standard permanganate solution can, in embodiments, be a potassium permanganate solution. The set reaction time can, in embodiments, be in a range from 10 to 30 minutes.

Figure 2:
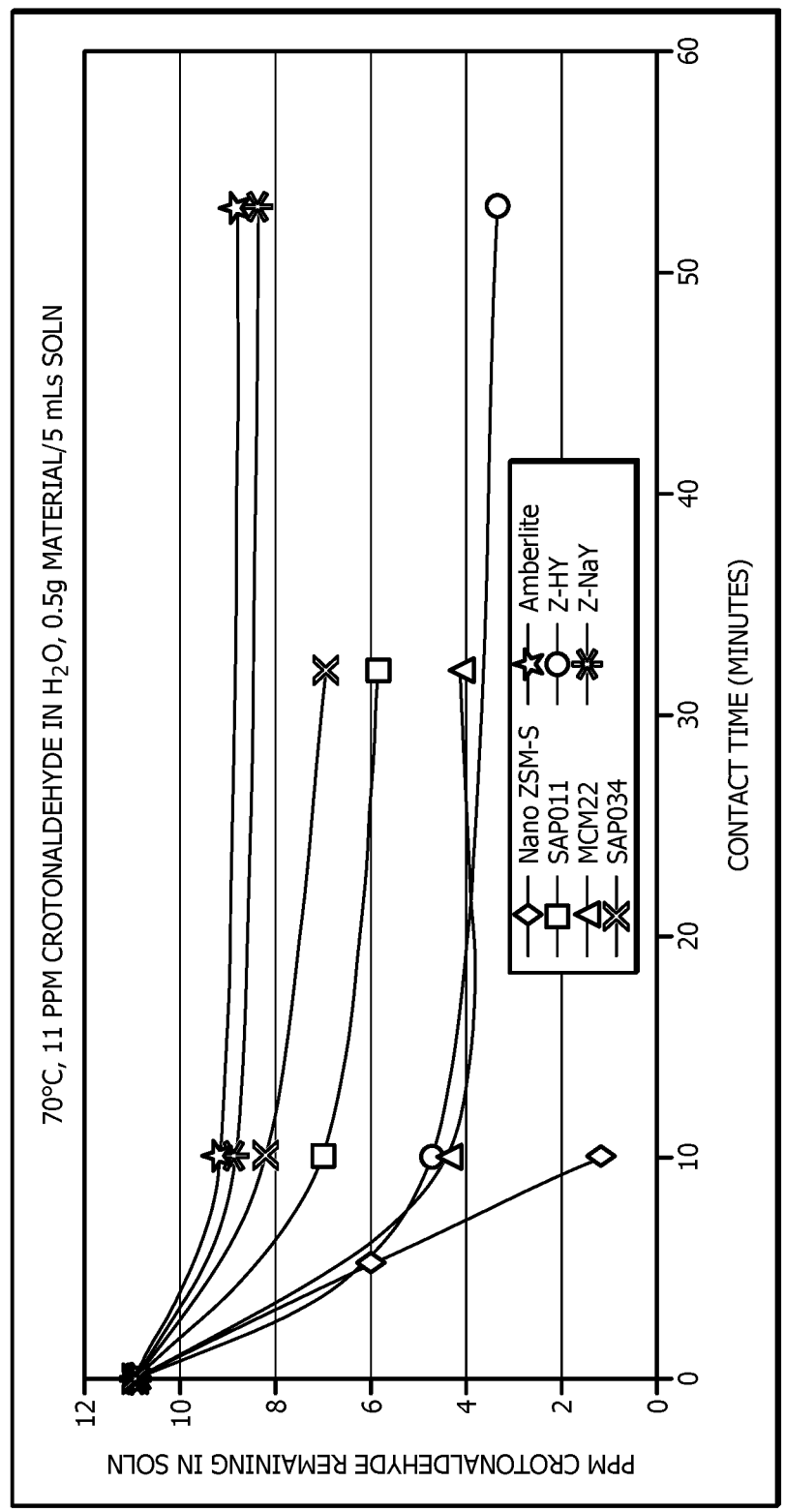
FIG. 2 is a plot of remaining crotonaldehyde equivalents as a function of contact time for experiments in Example 1.

FIG. 2 is a plot of the amount of crotonaldehyde remaining in solution (ppm) as a function of the contact time (min). The trend lines in FIG. 2 show that by the first sample point of 10 minutes, essentially complete crotonaldehyde removal has been achieved with nano ZSM•5 zeolite. In addition, a couple of conventional H—Y zeolites (e.g., Z—HY zeolite), and silicates show moderate removal while other agents such as silicoaluminophosphates (e.g., SAPO-11, SAPO-34), Na—Y zeolite (Z—Na—Y) and a weakly acidic cation exchange resin (e.g., AMBERLITE®) show removal efficiency ranging from none to poor. Further trials showed that nano ZSM-5 rapidly removes crotonaldehyde at room temperature and subsequent experiments were carried out without any heating. The silicoaluminophosphate SAPO-34 did not show substantial removal ability from a decanter light phase-type composition.

Figure 3:
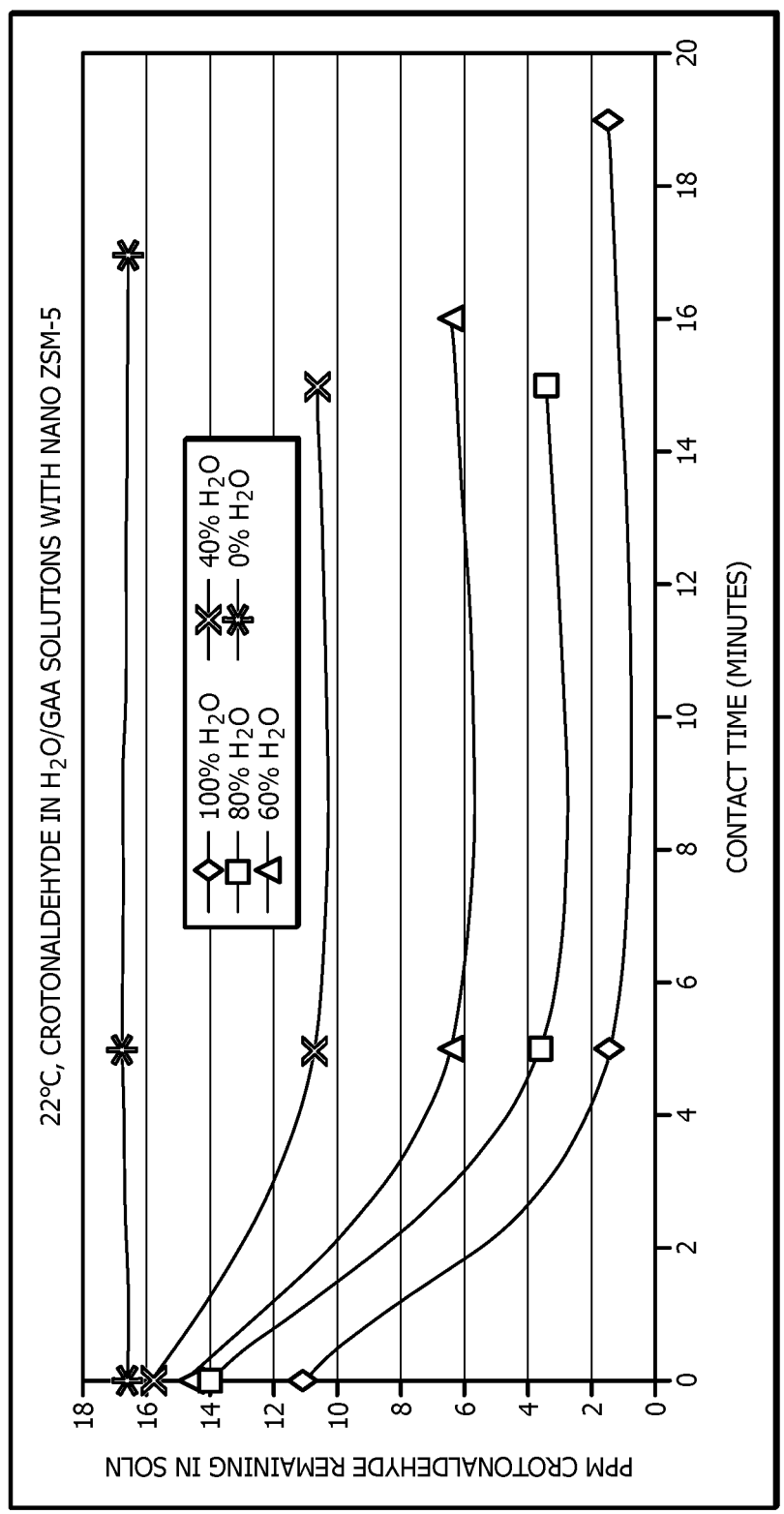
FIG. 3 is a plot of remaining crotonaldehyde equivalents as a function of contact time for experiments in Example 2.

Example 2: Room Temperature Experiments with PPM Levels of Oxidizable Impurities In a further study, a systematic investigation of the effect of the nature of the solvent (100/0 weight percent (wt %) $H_2O/GAA$ to 0/100 wt % $H_2O/GAA$) was carried out. Crotonaldehyde standards were prepared in mixed $H_2O/GAA$ solutions. As GAA itself contains significant oxidizable impurities, it was not possible to ensure precisely the same starting oxidizable impurity content in every standard, and starting impurity concentrations ranged from 11 to 17 crotonaldehyde equivalents as determined by UV/Vis. Removal efficiencies with nano-ZSM-5 are shown in FIG. 3 (similar loading in all experiments).

The data indicate decreasing removal efficiency with decreasing water content of the solution. However, good removal efficiency is possible with water concentration as low as 40%. These data indicate that permanganate reducing compounds can be removed from intermediate, water-containing GAA process streams.

Example 3: Room Temperature Experiments at Weight Percent Levels of Oxidizable Impurities and Ten Minute Contact Times The system and method of this disclosure may be utilized for the removal of oxidizable impurities from intermediate streams such as a decanter light phase or a distilled decanter light phase. While the product acetic acid stream (e.g., stream 156, 171) contains only ppm levels of oxidizable impurities (e.g., principally crotonaldehyde), intermediate streams, such as a decanter light phase 139, 139a, 139a' or distilled decanter light phase 139b', which may be treated via this disclosure can contain low weight percent (e.g., up to 10 wt %) levels of oxidizable impurities (e.g., principally acetaldehyde).

Streams comprising 2.2 weight percent acetaldehyde in water were contacted with various materials at room temperature (e.g., 22° C.). The materials were contacted with the aqueous acetaldehyde solutions at a ratio of 9 grams of removal material per 1 gram of acetaldehyde. The percent acetaldehyde removal after 10 minutes of contact at 22° C. for each material studied is tabulated in Table 1.

TABLE 1

| Material | Percent Acetaldehyde Removal |
| --- | --- |
| AMBERLYST ® 15 | 5 |
| SAPO-11 | 5 |
| SAPO-34 | 11 |
| MCM-22 | 12 |
| AMBERLITE ® IR120 | 19 |
| ZSM-5-H-26 | 51 |

The data in Table 1 indicate that the ability of ZSM-5 to remove oxidizable impurities from ppm level oxidizable impurity containing aqueous solutions is maintained when the solutions comprise impurities at the weight percent level.

Compositions comprising various ratios of water and acetic acid (e.g., 100/0 weight percent (wt %) $H_2O/GAA$ to 33/67 wt % $H_2O/GAA$) were contacted with nano ZSM-5. The aqueous solutions of acetic acid were prepared with 2.2 wt % acetaldehyde, and the ratio of oxidizable impurity (i.e., acetaldehyde) to material (i.e., ZSM-5) was 1 gram acetaldehyde to 9 grams of ZSM-5. The percent acetaldehyde removed after 10 minutes at 22° C. is tabulated in Table 2.

TABLE 2

| Solvent (wt %) | | Acetaldehyde Removal (wt %) | |
| --- | --- | --- | --- |
| $H_2O$ | Acetic Acid | Run 1 | Run 2 |
| 100 | 0 | 51 | 57 |
| 80 | 20 | 30 | 41 |
| 60 | 40 | 29 | 23 |
| 33 | 67 | 14 | 21 |

As shown for ppm levels of oxidizable impurities in the data in FIG. 3, the data in Table 2 above indicate effective removal of wt % levels of oxidizable impurities via ZSM-5.

Example 4: Room Temperature Experiments at Weight Percent Levels of Oxidizable Impurities and One Minute Contact Times Two vials containing five (5) mLs of 1.5 weight percent acetaldehyde (HAc) in water solution were added 0.6 g amounts of various adsorbent materials at room temperature (e.g., 22° C.). The slurries were briefly shaken, and then sampled at the one minute mark when the remaining acetaldehyde concentration in solution was determined via FTIR spectroscopy. The materials were contacted with the aqueous acetaldehyde solutions at a ratio of 8.5 grams of removal material (i.e., adsorbent) per 1 gram of acetaldehyde. The various materials tested, a description thereof, the silica to alumina (Si/Al) ratio thereof, the surface area (SA) in $m^2/g$, the median particle size, and the weight percent acetaldehyde removal after one minute of contact at 22° C. for each material studied are tabulated in Table 3.

TABLE 3

| Material | Description | Si/Al | SA ($m^2/g$) | Particle Size | % HAc Removal (1 min.) |
|---|---|---|---|---|---|
| AMBERLYST ® 15 | Strong Acid Resin, Crosslinked | NA | ~40 | <300 µm | 5 |
| AMBERLITE ™ IR120H | Strong Acid Resin, Gel | NA | Unk.[a] | 600-800 µm | 20 |
| AMBERLITE ™ CG50 | Weak Acid Resin, Crosslinked | NA | Unk.[a] | 75-150 µm | 17 |
| Aldrich Zeolite HY | Y Zeolite, Na Form | >5 | ~600 | ~6 µm | 1 |
| Alfa Aesar Zeolite HY | Y Zeolite, H+ Form | 30 | ~600 | ~6 µm | 26 |
| ZSM-22 | Zeolite, H+ Form | 65-80 | >180 | Unk[a] | 28 |
| ZSM 5-38 | Zeolite, H+ Form | 38 | >380 | 2 µm | 42 |
| Nano ZSM 5-26 | Zeolite, H+ Form | 26 | 362 | 300 nm | 36 |
| Nano ZSM 5-91 | Zeolite, H+ Form | 91 | 362 | 300 nm | 55 |
| Nano ZSM 5-371 | Zeolite, H+ Form | 371 | 362 | 300 nm | 63 |
| MCM-41 ($SiO_2$) | Silicate | ~Infinity | >850 | 100-1000 nm | 20 |
| SAPO 11 | Silicoaluminophosphate | 0.12 | >180 | Unk.[a] | 5 |
| SAPO 34 | Silicoaluminophosphate | 0.25 | >550 | 2 µm | 11 |

[a]Unknown

It can be seen from the data in Table 3 that at weight percent concentrations of impurities (e.g., 1.5 weight percent acetaldehyde), nanozeolites Nano ZSM 5-26, Nano ZSM 5-91, and Nano ZSM 5-371, and zeolite ZSM 5-38 provided greater than 30 percent acetaldehyde removal by one minute contact time. The nanozeolites Nano ZSM 5-91, and Nano ZSM 5-371, having the higher Si/Al ratios (i.e., 91 and 371, respectively) provided the higher acetaldehyde removal at one minute, with removal percentages of 55 and 63%, respectively.

Example 5: Room Temperature Experiments at Weight Percent Levels of Oxidizable Impurities, One Minute Contact Times, and Various Loadings of Adsorbent Two vials containing five (5) mLs of 1.5 weight percent acetaldehyde (HAc) in water solution were added various mass loadings of four adsorbent materials (Nano ZSM-5-26, Nano ZSM-5-91, Nano ZSM-5-371, and ZSM-5-38) at room temperature (e.g., 22° C.). The slurries were briefly shaken, and then sampled at the one minute mark, when the remaining acetaldehyde concentration in solution was determined via FTIR spectroscopy. Each of the four materials tested was contacted with the aqueous acetaldehyde solutions at ratios of 0.24, 0.12, and 0.07 gram of acetaldehyde per gram of removal material (i.e., adsorbent). The materials tested, the loading (gram HAc per gram adsorbent), and the percent acetaldehyde removal after one minute of contact at 22° C. for each material studied are tabulated in Table 4.

TABLE 4

| Material | Loading (g HAc/g Adsorbent) | % HAc Removed |
|---|---|---|
| Nano ZSM-5-26 | 0.24 | 24 |
| Nano ZSM-5-26 | 0.12 | 36 |
| Nano ZSM-5-26 | 0.07 | 58 |
| Nano ZSM-5-91 | 0.24 | 30 |
| Nano ZSM-5-91 | 0.12 | 56 |
| Nano ZSM-5-91 | 0.07 | 73 |
| Nano ZSM-5-371 | 0.24 | 28 |
| Nano ZSM-5-371 | 0.12 | 63 |
| Nano ZSM-5-371 | 0.07 | 77 |
| ZSM-5-38 | 0.24 | 27 |
| ZSM-5-38 | 0.12 | 42 |
| ZSM-5-38 | 0.07 | 54 |

As seen in the data in Table 4, the acetaldehyde removal increases with the loading of adsorbent material.

Example 6: Elevated Temperature Experiments at Weight Percent Levels of Oxidizable Impurities and One Minute Contact Times At time 0, five (5) mLs of 1.5 weight percent acetaldehyde (HAc) in water solution heated in oil bath to 53° C. was added to septum vials containing 0.6 g of various adsorbent materials. (The septum vials were also heated to 53° C.) The slurries were briefly shaken, and then sampled at the one and fourteen (14) minute marks when the remaining acetaldehyde concentrations in solution were determined via FTIR spectroscopy. The materials were contacted with the aqueous acetaldehyde solutions at a ratio of 0.12 gram of acetaldehyde per gram of adsorbent. The various materials tested, and the weight percent acetaldehyde removal after one minute or fourteen minutes of contact at 22° C. and at 53° C. for each material studied are tabulated in Table 5.

TABLE 5

| Material | Temp, ° C. | Time, min. | % HAc Removed |
| --- | --- | --- | --- |
| Nano ZSM-5-26 | 22 | 1 | 36 |
| Nano ZSM-5-26 | 22 | 14 | 35 |
| Nano ZSM-5-26 | 53 | 1 | 43 |
| Nano ZSM-5-26 | 53 | 14 | 45 |
| Nano ZSM-5-371 | 22 | 1 | 63 |
| Nano ZSM-5-371 | 22 | 14 | ND |
| Nano ZSM-5-371 | 53 | 1 | 62 |
| Nano ZSM-5-371 | 53 | 14 | ND |
| Alfa Aesar Zeolite HY | 22 | 1 | 26 |
| Alfa Aesar Zeolite HY | 22 | 14 | 28 |
| Alfa Aesar Zeolite HY | 53 | 1 | 29 |
| Alfa Aesar Zeolite HY | 53 | 14 | 28 |
| AMBERLITE ™ CG50 | 22 | 1 | 17 |
| AMBERLITE ™ CG50 | 22 | 14 | 18 |
| AMBERLITE ™ CG50 | 53 | 1 | 21 |
| AMBERLITE ™ CG50 | 53 | 14 | 22 |

As can be seen from the data in Table 5, in most cases, substantially all of the acetaldehyde that will be removed is removed by the one minute mark, with some samples actually showing greater removal at one minute than fourteen minutes. Additionally, higher temperature provided for a 19 and 29% greater acetaldehyde removal at 1 and 14 minutes, respectively, for Nano ZSM-5-26, a 1.6% lower acetaldehyde removal at 1 minute for Nano ZSM-5-371, a 12 and 0% greater acetaldehyde removal at 1 and 14 minutes, respectively, for Alfa Aesar Zeolite HY, and a 24 and 22% greater acetaldehyde removal at 1 and 14 minutes, respectively, for AMBERLITE™ CG50. Thus, in all cases, at least 75% of the acetaldehyde removed at the higher temperature was removed at the lower temperature, with no or reduced acetaldehyde removed at the higher temperature relative to the lower temperature for two of the cases.

ADDITIONAL DISCLOSURE

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and unambiguously defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method of producing acetic acid, the method comprising: reacting methanol and/or methanol derivatives with carbon monoxide in the presence of a liquid reaction medium under carbonylation conditions to form a carbonylation product comprising acetic acid and one or more oxidizable impurities; and contacting at least a portion of the carbonylation product or a derivative thereof with an adsorbent at adsorption conditions to provide a purified product comprising a reduced concentration of at least one of the one or more oxidizable impurities relative to a concentration thereof in the at least a portion of the carbonylation product or the derivative thereof.

B: An acetic acid production system comprising: a carbonylation reactor for contacting methanol with carbon monoxide in the presence of a liquid reaction medium under carbonylation conditions to form a carbonylation product comprising acetic acid and one or more oxidizable impurities; and an adsorbent vessel in which at least a portion of the carbonylation product or a derivative thereof can be contacted with an adsorbent at adsorption conditions to provide a purified product having a reduced concentration of at least one of the one or more oxidizable impurities relative to a concentration thereof in the at least a portion of the carbonylation product or the derivative thereof.

Each of embodiments A and B may have one or more of the following additional elements:

Element 1: wherein the one or more oxidizable impurities are selected from saturated carbonyl compounds, unsaturated carbonyl compounds, aldol condensation products thereof, propionic acid, or combinations thereof. Element 2: wherein the one or more oxidizable impurities are selected from acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof. Element 3: wherein the one or more oxidizable impurities comprise primarily acetaldehyde. Element 4: wherein the adsorbent comprises a zeolite, an acidic ion exchange resin, a silicate, or a combination thereof. Element 5: wherein the zeolite comprises a nanozeolite, an H—Y zeolite, or a combination thereof. Element 6: wherein the zeolite comprises a nanozeolite having an average particle size of less than or equal to 300, 250, or 200 nm. Element 7: wherein the adsorbent comprises Nano ZSM-5, MCM-22, Z—HY zeolite, or a combination thereof. Element 8: wherein the adsorbent has a silica to alumina (Si/Al) molar ratio in a range of from 1/1 to 400/1, from 10/1 to 400/1, from 20/1 to 400/1, or greater than or equal to 20/1, 30/1, 40/1, 50/1, 60/1, 70/1, 80/1, 90/1, or 100/1. Element 9: wherein the contacting of the at least a portion of the carbonylation product or the derivative thereof is effected in the presence of at least 30, 40, 50, 60 70, 80, or 85 weight percent (wt %) water. Element 10: wherein the at least a portion of the carbonylation product or the derivative thereof comprises at least 30, 40, 50, 60, 70, 80, or 85 wt % water, wherein water is added such that the contacting of the at least a portion of the carbonylation product or the derivative thereof is effected in the presence of at least 30, 40, 50, 60, 70, 80, or 85 wt % water, or a combination thereof. Element 11: wherein the at least a portion of the carbonylation product or the derivative thereof comprises less than or equal to 70, 60, 50, 40, 30, 20, or 10 wt % acetic acid. Element 12: further comprising: flashing the carbonylation product to separate a vapor fraction comprising a majority of the acetic acid in the carbonylation product from a liquid fraction; subjecting the vapor fraction to a light ends distillation to separate a lights overhead stream having a boiling point less than that of acetic acid and an acetic acid stream; introducing the lights overhead stream into a separator to form, relative to each stream, a light aqueous phase comprising acetic acid and water, and a heavy organic phase; or a combination thereof, wherein the at least a portion of the carbonylation product or the derivative thereof contacted with the adsorbent comprises at least a portion of the light aqueous phase. Element 13: further comprising: flashing the carbonylation product to separate a vapor fraction comprising a majority of the acetic acid in the carbonylation product from a liquid fraction; subjecting the vapor fraction to a light ends distillation to separate a lights overhead stream having a boiling point less than that of acetic acid and an acetic acid stream; and passing the acetic acid stream through a drying column to remove water therefrom, thus providing a bottoms dried acetic acid stream and an overhead drying column water stream, wherein the contacting of the at least a portion of the carbonylation product or the derivative thereof with the adsorbent comprises contacting at least a portion of the overhead drying column water stream with the adsorbent. Element 14: further comprising subjecting the bottoms dried acetic acid stream to a heavy ends distillation to produce a crude acetic acid stream and a heavies bottoms stream having a boiling point greater than that of acetic acid. Element 15: further comprising: flashing the carbonylation product to separate a vapor fraction comprising a majority of the acetic acid in the carbonylation product from a liquid fraction; subjecting the vapor fraction to a light ends distillation to separate a lights overhead stream having a boiling point less than that of acetic acid and an acetic acid stream; introducing the lights overhead stream into a separator to form, relative to each stream, a light aqueous phase comprising acetic acid and water, and a heavy organic phase; and subjecting the light aqueous phase to distillation, aqueous extraction, or both, thus providing a light phase aqueous solution comprising oxidizable impurities; subjecting the heavy organic phase to distillation and aqueous extraction, thus providing a heavy phase aqueous solution comprising oxidizable impurities; or both, wherein the at least a portion of the carbonylation product or the derivative thereof contacted with the adsorbent comprises the light phase aqueous solution, the heavy phase aqueous solution, or both. Element 16: wherein the contacting is performed at a temperature of room temperature, or less than or equal to 100° C., 90° C., 80° C., 70° C., 60° C., 50° C., 40° C. 30° C., 25° C., or 20° C. Element 17: wherein the carbonylation product comprises greater than or equal to 0.05 wt % of one or more oxidizable impurities. Element 18: wherein the at least a portion of the carbonylation product or the derivative thereof contacted with the adsorbent comprises at least 0.05, 10, or 50 wt % oxidizable impurities, and wherein the purified product comprises less than or equal to 0.01, 3, or 20 wt % oxidizable impurities. Element 19: wherein the purified product comprises at least 10, 60, or 80 percent less oxidizable impurities than the at least a portion of the carbonylation product or the derivative thereof contacted with the adsorbent. Element 20: wherein contacting the at least a portion of the carbonylation product or the derivative thereof with the adsorbent comprises passing the carbonylation product or the derivative thereof through a fixed bed of the adsorbent to remove oxidizable impurities therefrom. Element 21: wherein the contacting comprises passing the carbonylation product or the derivative thereof through the fixed bed at a flow rate in the range of from 0.1 to 50 bed volumes per hour (BV/h), from 1 to 40 BV/h, or from 5 to 30 BV/h, wherein a flow rate of 1 BV/h means that a quantity of the carbonylation product or the derivative thereof equal to a volume occupied by the fixed bed of the adsorbent passes through the fixed bed in one hour. Element 22: wherein the contacting is effected via a static slurry bed or other batch process, and for a contact time of less than or equal to 60, 50, 40, 30, 20, 10, 9, 8, 7, 6, 5, 4, 3, 2, or 1 minute. Element 23: wherein a mass ratio of the carbonylation product or the derivative thereof to the adsorbent is in the range of from 2 to 15 grams of the carbonylation product or the derivative thereof to grams adsorbent, from 2 to 10 grams of the carbonylation product or the derivative thereof to grams adsorbent, or from 3 to 8 grams of the carbonylation product or the derivative thereof to grams adsorbent. Element 24: wherein the liquid reaction medium comprises: a carbonylation catalyst selected from rhodium catalysts, iridium catalysts and palladium catalysts; and water at a concentration in a range of from 1 wt % to 14 wt %, based on the total weight of the liquid reaction medium. Element 25: wherein the carbonylation product comprises greater than or equal to 0.02, 2, or 10 wt % of the one or more oxidizable impurities, wherein the purified product comprises less than or equal to 0.01, 1 or 3 wt % of the at least one of the one or more oxidizable impurities, or a combination thereof. Element 26: further comprising: a flash vessel operable to separate the carbonylation product into a liquid fraction and a vapor fraction comprising acetic acid and one or more oxidizable impurities; a light ends distillation column configured to separate the vapor fraction into a lights overhead stream having a boiling point less than that of acetic acid and an acetic acid stream; a separator operable to separate the lights overhead stream into a light aqueous phase comprising acetic acid and water, and a heavy organic phase; or a combination thereof, wherein the adsorbent vessel is fluidly connected with the flash vessel, the light ends distillation column, the separator, or a combination thereof, whereby the at least a portion of the carbonylation product or the derivative thereof contacted with the adsorbent comprises at least a portion of the vapor fraction, at least a portion of the lights overhead stream, at least a portion of the light aqueous phase, at least a portion of the heavy organic phase, or a combination thereof. Element 27: further comprising: a flash vessel operable to separate the carbonylation product into a liquid fraction and a vapor fraction comprising acetic acid and one or more impurities; a light ends distillation column configured to separate the vapor fraction into a lights overhead stream having a boiling point less than that of acetic acid and an acetic acid stream; and a drying column configured to remove water from the acetic acid stream, thus providing a dried acetic acid stream and a drying column water stream, wherein the adsorbent vessel is fluidly connected with the flash vessel, the light ends distillation column, the drying column, or a combination thereof, whereby the at least a portion of the carbonylation product or the derivative thereof contacted with the adsorbent comprises at least a portion of the vapor fraction, at least a portion of the lights overhead stream, at least a portion of the drying column water stream, or a combination thereof. Element 28: further comprising a heavy ends distillation column for subjecting the dried acetic acid stream to distillation and thus produce a crude acetic acid stream and a heavies bottoms stream having a boiling point greater than that of acetic acid. Element 29: further comprising: a flash vessel operable to separate the carbonylation product into a liquid fraction and a vapor fraction; a light ends distillation column configured to separate the vapor fraction into a lights overhead stream having a boiling point of less than that of acetic acid and an acetic acid stream; a separator operable to form, relative to each stream, a light aqueous phase comprising acetic acid and water, and a heavy organic phase from the lights overhead stream; and a distillation column, an aqueous extraction unit, or both, configured to provide an aqueous solution comprising oxidizable impurities from the light aqueous phase comprising acetic acid and water, the heavy organic phase, or both, wherein the at least a portion of the carbonylation product or the derivative thereof introduced into the adsorbent vessel comprises the aqueous solution. Element 30: wherein the adsorbent vessel provides a contact time of less than or equal to 60, 50, 40, 30, 20, 10, 9, 8, 7, 6, 5, 4, 3, 2, or 1 minute.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method of producing acetic acid, the method comprising:
    reacting methanol and/or methanol derivatives with carbon monoxide in the presence of a liquid reaction medium under carbonylation conditions to form a carbonylation product comprising acetic acid and one or more oxidizable impurities; and
    contacting at least a portion of the carbonylation product or a derivative thereof with an adsorbent at adsorption conditions to provide a purified product comprising a reduced concentration of at least one of the one or more oxidizable impurities relative to a concentration thereof in the at least a portion of the carbonylation product or the derivative thereof,
    wherein the absorbent comprises a nanozeolite, and wherein the nanozeolite has an average particle size of less than or equal to 300 nm.

2. The method of claim 1, wherein the one or more oxidizable impurities are selected from saturated carbonyl compounds, unsaturated carbonyl compounds, aldol condensation products thereof, propionic acid, or combinations thereof.

3. The method of claim 2, wherein the one or more oxidizable impurities are selected from acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof.

4. The method of claim 1, wherein the adsorbent further comprises an acidic ion exchange resin, a silicate, or a combination thereof.

5. The method of claim 4, wherein the nanozeolite has an average particle size of less than or equal to 250 nm.

6. The method of claim 1, wherein the adsorbent has a silica to alumina (Si/Al) molar ratio of greater than or equal to 20/1.

7. The method of claim 1, wherein the contacting of the at least a portion of the carbonylation product or the derivative thereof is effected in the presence of at least 30 weight percent (wt %) water, wherein the at least a portion of the carbonylation product or the derivative thereof comprises less than or equal to 70 wt % acetic acid, or both.

8. The method of claim 1 further comprising:
    flashing the carbonylation product to separate a vapor fraction comprising a majority of the acetic acid in the carbonylation product from a liquid fraction;
    subjecting the vapor fraction to a light ends distillation to separate a lights overhead stream having a boiling point less than that of acetic acid and an acetic acid stream;
    introducing the lights overhead stream into a separator to form, relative to each stream, a light aqueous phase comprising acetic acid and water, and a heavy organic phase;
    or a combination thereof,
    wherein the at least a portion of the carbonylation product or the derivative thereof contacted with the adsorbent comprises at least a portion of the light aqueous phase.

9. The method of claim 1 further comprising:
    flashing the carbonylation product to separate a vapor fraction comprising a majority of the acetic acid in the carbonylation product from a liquid fraction;
    subjecting the vapor fraction to a light ends distillation to separate a lights overhead stream having a boiling point less than that of acetic acid and an acetic acid stream; and
    passing the acetic acid stream through a drying column to remove water therefrom, thus providing a bottoms dried acetic acid stream and an overhead drying column water stream,
    wherein the contacting of the at least a portion of the carbonylation product or the derivative thereof with the adsorbent comprises contacting at least a portion of the overhead drying column water stream with the adsorbent.

10. The method of claim 1 further comprising:
    flashing the carbonylation product to separate a vapor fraction comprising
    a majority of the acetic acid in the carbonylation product from a liquid fraction;
    subjecting the vapor fraction to a light ends distillation to separate a lights overhead stream having a boiling point less than that of acetic acid and an acetic acid stream;
    introducing the lights overhead stream into a separator to form, relative to each stream, a light aqueous phase comprising acetic acid and water, and a heavy organic phase; and
    subjecting the light aqueous phase to distillation, aqueous extraction, or both, thus providing a light phase aqueous solution comprising oxidizable impurities; subjecting the heavy organic phase to distillation and aqueous extraction, thus providing a heavy phase aqueous solution comprising oxidizable impurities; or both,
wherein the at least a portion of the carbonylation product or the derivative thereof contacted with the adsorbent comprises the light phase aqueous solution, the heavy phase aqueous solution, or both.

11. The method of claim 1, wherein the contacting is performed at a temperature of room temperature, or less than or equal to 70° C., wherein the at least a portion of the carbonylation product or the derivative thereof contacted with the adsorbent comprises at least 0.05 weight percent (wt %) oxidizable impurities, wherein the purified product comprises less than or equal to 0.01 wt % oxidizable impurities, or a combination thereof.

12. An acetic acid production system comprising:
a carbonylation reactor for contacting methanol with carbon monoxide in the presence of a liquid reaction medium under carbonylation conditions to form a carbonylation product comprising acetic acid and one or more oxidizable impurities; and
an adsorbent vessel in which at least a portion of the carbonylation product or a derivative thereof can be contacted with an adsorbent at adsorption conditions to provide a purified product having a reduced concentration of at least one of the one or more oxidizable impurities relative to a concentration thereof in the at least a portion of the carbonylation product or the derivative thereof
wherein the absorbent comprises a nanozeolite, and wherein the nanozeolite has an average particle size of less than or equal to 300 nm.

13. The system of claim 12, wherein the adsorbent further comprises an acidic ion exchange resin, a silicate, or a combination thereof.

14. The system of claim 13, wherein the absorbent comprises an H—Y zeolite and, wherein the nanozeolite has an average particle size of less than or equal to 250 nm.

15. The system of claim 12, wherein the adsorbent has a silica to alumina (Si/Al) molar ratio of greater than or equal to 20/1.

16. The system of claim 12, wherein the at least a portion of the carbonylation product or the derivative thereof comprises at least 30 weight percent (wt %) water, wherein the at least a portion of the carbonylation product or the derivative thereof comprises less than or equal to 70 wt % acetic acid, or both.

17. The system of claim 12, wherein the carbonylation product comprises greater than or equal to 0.02 weight percent (wt %) of the one or more oxidizable impurities, wherein the purified product comprises less than or equal to 0.01 wt % of the one or more oxidizable impurities, or a combination thereof.

18. The system of claim 12 further comprising:
a flash vessel operable to separate the carbonylation product into a liquid fraction and a vapor fraction comprising acetic acid and one or more oxidizable impurities;
a light ends distillation column configured to separate the vapor fraction into a lights overhead stream having a boiling point less than that of acetic acid and an acetic acid stream;
a separator operable to separate the lights overhead stream into a light aqueous phase comprising acetic acid and water, and a heavy organic phase;
or a combination thereof,
wherein the adsorbent vessel is fluidly connected with the flash vessel, the light ends distillation column, the separator, or a combination thereof, whereby the at least a portion of the carbonylation product or the derivative thereof contacted with the adsorbent comprises at least a portion of the vapor fraction, at least a portion of the lights overhead stream, at least a portion of the light aqueous phase, at least a portion of the heavy organic phase, or a combination thereof.

19. The system of claim 12 further comprising:
a flash vessel operable to separate the carbonylation product into a liquid fraction and a vapor fraction comprising acetic acid and one or more impurities;
a light ends distillation column configured to separate the vapor fraction into a lights overhead stream having a boiling point less than that of acetic acid and an acetic acid stream; and
a drying column configured to remove water from the acetic acid stream, thus providing a dried acetic acid stream and a drying column water stream,
wherein the adsorbent vessel is fluidly connected with the flash vessel, the light ends distillation column, the drying column, or a combination thereof, whereby the at least a portion of the carbonylation product or the derivative thereof contacted with the adsorbent comprises at least a portion of the vapor fraction, at least a portion of the lights overhead stream, at least a portion of the drying column water stream, or a combination thereof.

20. The system of claim 12 further comprising:
a flash vessel operable to separate the carbonylation product into a liquid fraction and a vapor fraction;
a light ends distillation column configured to separate the vapor fraction into a lights overhead stream having a boiling point of less than that of acetic acid and an acetic acid stream;
a separator operable to form, relative to each stream, a light aqueous phase comprising acetic acid and water, and a heavy organic phase from the lights overhead stream; and
a distillation column, an aqueous extraction unit, or both, configured to provide an aqueous solution comprising oxidizable impurities from the light aqueous phase comprising acetic acid and water, the heavy organic phase, or both,
wherein the at least a portion of the carbonylation product or the derivative thereof introduced into the adsorbent vessel comprises the aqueous solution.

* * * * *